US009315775B2

(12) United States Patent
Joyner et al.

(10) Patent No.: US 9,315,775 B2
(45) Date of Patent: Apr. 19, 2016

(54) METHODS AND MATERIALS FOR PROLONGING USEFUL STORAGE OF RED BLOOD CELL PREPARATIONS AND PLATELET PREPARATIONS

(71) Applicant: Mayo Foundation for Medical Education and Research, Rochester, MN (US)

(72) Inventors: Michael J. Joyner, Rochester, MN (US); Daniel G. Ericson, Rochester, MN (US)

(73) Assignees: Mayo Foundation for Medical Education and Research, Rochester, MN (US); Dynasil Biomedical Corporation, Watertown, MA (US)

( * ) Notice: Subject to any disclaimer, the term of this patent is extended or adjusted under 35 U.S.C. 154(b) by 0 days.

(21) Appl. No.: 14/307,698

(22) Filed: Jun. 18, 2014

(65) Prior Publication Data

US 2014/0295402 A1    Oct. 2, 2014

Related U.S. Application Data

(63) Continuation of application No. 13/816,775, filed as application No. PCT/US2012/029510 on Mar. 16, 2012, now abandoned.

(60) Provisional application No. 61/453,455, filed on Mar. 16, 2011, provisional application No. 61/562,331, filed on Nov. 21, 2011.

(51) Int. Cl.
*A01N 1/02* (2006.01)
*C12N 5/078* (2010.01)

(52) U.S. Cl.
CPC ............ *C12N 5/0644* (2013.01); *A01N 1/0226* (2013.01); *A01N 1/0263* (2013.01)

(58) Field of Classification Search
None
See application file for complete search history.

(56) References Cited

U.S. PATENT DOCUMENTS

| | | |
|---|---|---|
| 3,729,947 A | 5/1973 | Higuchi |
| 4,280,497 A | 7/1981 | Warner et al. |
| 4,455,299 A | 6/1984 | Grode |
| 4,496,361 A | 1/1985 | Kilkson |
| 4,588,401 A | 5/1986 | Kilkson |
| 4,670,013 A | 6/1987 | Barnes et al. |
| 4,695,460 A | 9/1987 | Holme |
| 4,828,976 A | 5/1989 | Murphy |
| 4,992,363 A | 2/1991 | Murphy |
| 4,994,367 A | 2/1991 | Bode et al. |
| 5,147,776 A | 9/1992 | Koerner |
| 5,248,506 A | 9/1993 | Holme et al. |
| 5,250,303 A | 10/1993 | Meryman et al. |
| 5,262,180 A | 11/1993 | Orlando et al. |
| 5,476,764 A | 12/1995 | Bitensky |
| 5,487,971 A | 1/1996 | Holme et al. |
| 5,569,579 A | 10/1996 | Murphy |
| 5,576,213 A | 11/1996 | Stossel et al. |
| 5,622,867 A | 4/1997 | Livesey et al. |
| 5,624,794 A | 4/1997 | Bitensky et al. |
| 5,667,769 A | 9/1997 | Kueckens et al. |
| 5,772,960 A | 6/1998 | Ito et al. |
| 5,789,151 A | 8/1998 | Bitensky et al. |
| 6,087,087 A | 7/2000 | Yonetani et al. |
| 6,162,396 A | 12/2000 | Bitensky et al. |
| 6,221,669 B1 | 4/2001 | Livesey et al. |
| 6,315,767 B1 | 11/2001 | Dumont et al. |
| 6,413,200 B1 | 7/2002 | Jorgensen et al. |
| 6,413,713 B1 | 7/2002 | Serebrennikov |
| 6,468,732 B1 | 10/2002 | Malin et al. |
| RE38,203 E | 7/2003 | Kelly |
| 6,730,267 B2 | 5/2004 | Stringer et al. |
| 6,828,090 B2 | 12/2004 | Lucas et al. |
| 7,202,020 B2 | 4/2007 | Lucas et al. |
| 7,241,282 B2 | 7/2007 | Stossel et al. |
| 7,323,295 B2 | 1/2008 | Shaklai et al. |

(Continued)

FOREIGN PATENT DOCUMENTS

| | | |
|---|---|---|
| CN | 103702557 A | 4/2014 |
| EP | 114372 A2 | 8/1984 |

(Continued)

OTHER PUBLICATIONS

Kilkson et al. "Platelet Metabolism During Storage of Platelet Concentrates at 22 C" (1984) Blood, vol. 64, No. 2: 406-414.*
"U.S. Appl. No. 13/816,775, Final Office Action mailed Apr. 25, 2014", 13 pgs.
"U.S. Appl. No. 13/816,775, Non Final Office Action mailed Jan. 16, 2014", 16 pgs.
"U.S. Appl. No. 13/816,775, Response filed Arp. 15, 2014 to Non Final Office Action mailed Jan. 16, 2014", 16 pgs.
"U.S. Appl. No. 13/816,775, Response filed Aug. 13, 2013 to Restriction Requirement mailed Jun. 13, 2013", 8 pgs.
"U.S. Appl. No. 13/816,775, Restriction Requirement mailed Jun. 13, 2013", 7 pgs.
"Chinese Application Serial No. 201280023194.6, Amendment filed Feb. 17, 2014", 31 pgs.

(Continued)

*Primary Examiner* — Robert Yamasaki
*Assistant Examiner* — Teresa E Knight
(74) *Attorney, Agent, or Firm* — Schwegman, Lundberg & Woessner, P.A.

(57) ABSTRACT

This document provides methods and materials for enhancing the storage capabilities of red blood cell preparations. For example, methods and materials for using $CO_2$ to store red blood cells in a manner that (a) reduces the level of glucose or 2,3-DPG consumption of or reduces the level of 2,3-DPG production by a red blood cell preparation, (b) reduces the level of lactate formation by a red blood cell preparation, and/or (c) reduces the pH level of a red blood cell preparation are provided. Such methods and materials can result in prolonging the useful lifespan of the red blood cells of the red blood cell preparation. This document also provides methods and materials involved in prolonging useful storage of platelet preparations. For example, methods and materials for storing platelets in a manner that reduces platelet metabolism, that preserves platelet function, and/or that reduces the risk of bacterial contamination are provided.

19 Claims, 18 Drawing Sheets

(56) References Cited

U.S. PATENT DOCUMENTS

| | | |
|---|---|---|
| 7,531,133 B2 | 5/2009 | Hole et al. |
| 7,723,017 B2 | 5/2010 | Bitensky et al. |
| 7,858,295 B2 | 12/2010 | Stossel et al. |
| 7,964,338 B2 | 6/2011 | Sehgal et al. |
| 8,071,282 B2 | 12/2011 | Bitensky et al. |
| 8,158,339 B2 | 4/2012 | Ilyin et al. |
| 8,178,318 B2 | 5/2012 | Cheng et al. |
| 2003/0039638 A1 | 2/2003 | Bach et al. |
| 2003/0124504 A1 | 7/2003 | Bitensky et al. |
| 2003/0153074 A1 | 8/2003 | Bitensky et al. |
| 2004/0081580 A1 | 4/2004 | Hole et al. |
| 2004/0109903 A1 | 6/2004 | Shaklai et al. |
| 2004/0131703 A1 | 7/2004 | Bach et al. |
| 2004/0185036 A1 | 9/2004 | Stossel et al. |
| 2005/0019743 A1 | 1/2005 | Wagner et al. |
| 2005/0170019 A1 | 8/2005 | Roth |
| 2005/0208462 A1 | 9/2005 | Bitensky et al. |
| 2005/0277108 A1 | 12/2005 | Bitensky et al. |
| 2007/0003432 A1 | 1/2007 | Christensen et al. |
| 2008/0171021 A1 | 7/2008 | Bach et al. |
| 2008/0199845 A1 | 8/2008 | Rosiello et al. |
| 2008/0233554 A1 | 9/2008 | Sehgal et al. |
| 2009/0035386 A1 | 2/2009 | Matheis et al. |
| 2009/0074737 A1 | 3/2009 | Rosiello et al. |
| 2009/0110596 A1 | 4/2009 | Christensen et al. |
| 2009/0155763 A1 | 6/2009 | Rosiello et al. |
| 2009/0191537 A1 | 7/2009 | Mayaudon et al. |
| 2009/0246193 A1 | 10/2009 | Christensen |
| 2009/0253115 A1 | 10/2009 | Sehgal et al. |
| 2009/0263781 A1 | 10/2009 | Sehgal et al. |
| 2010/0080790 A1 | 4/2010 | Matthews et al. |
| 2010/0292200 A1 | 11/2010 | Kile et al. |
| 2011/0189151 A1 | 8/2011 | Stossel et al. |
| 2011/0223579 A1 | 9/2011 | Sehgal |
| 2012/0024156 A1 | 2/2012 | Yoshida et al. |
| 2012/0058558 A1 | 3/2012 | Sehgal |
| 2012/0077182 A1 | 3/2012 | Bitensky et al. |
| 2012/0100523 A1 | 4/2012 | Federspiel et al. |
| 2012/0107791 A1 | 5/2012 | Rosiello et al. |
| 2012/0115124 A1 | 5/2012 | Yoshida et al. |
| 2012/0129149 A1 | 5/2012 | Federspiel et al. |
| 2012/0196362 A1 | 8/2012 | Ilyin et al. |
| 2012/0225044 A9 | 9/2012 | Rosiello et al. |
| 2012/0225416 A1 | 9/2012 | Yoshida et al. |
| 2013/0143196 A1 | 6/2013 | Joyner et al. |

FOREIGN PATENT DOCUMENTS

| | | |
|---|---|---|
| EP | 142339 A1 | 5/1985 |
| EP | 281621 A1 | 9/1988 |
| EP | 330151 A2 | 8/1989 |
| EP | 387700 A1 | 9/1990 |
| EP | 494957 A1 | 7/1992 |
| EP | 510185 A1 | 10/1992 |
| EP | 649311 A1 | 4/1995 |
| EP | 684762 A1 | 12/1995 |
| EP | 775009 A1 | 5/1997 |
| EP | 786934 A2 | 8/1997 |
| EP | 830058 A1 | 3/1998 |
| EP | 853881 A2 | 7/1998 |
| EP | 981272 A1 | 3/2000 |
| EP | 1161143 B1 | 5/2004 |
| EP | 2077074 A2 | 7/2009 |
| EP | 2355860 A1 | 8/2011 |
| EP | 2389064 A1 | 11/2011 |
| EP | 2459247 A2 | 6/2012 |
| JP | 2007130503 A | 5/2007 |
| KR | 1020140033015 A | 3/2014 |
| WO | WO-8401292 A1 | 4/1984 |
| WO | WO-8502116 A1 | 5/1985 |
| WO | WO-8705468 A1 | 9/1987 |
| WO | WO-8801871 A1 | 3/1988 |
| WO | WO-9104659 A1 | 4/1991 |
| WO | WO-9208349 A1 | 5/1992 |
| WO | WO-9402015 A1 | 2/1994 |
| WO | WO-9418829 A1 | 9/1994 |
| WO | WO-9613158 A2 | 5/1996 |
| WO | WO-9615757 A1 | 5/1996 |
| WO | WO-9639026 A1 | 12/1996 |
| WO | WO-9730350 A1 | 8/1997 |
| WO | WO-9851147 A1 | 11/1998 |
| WO | WO-0209514 A1 | 2/2002 |
| WO | WO-0236136 A2 | 5/2002 |
| WO | WO-03043419 A1 | 5/2003 |
| WO | WO-03043571 A2 | 5/2003 |
| WO | WO-03094930 A1 | 11/2003 |
| WO | WO-03094936 A1 | 11/2003 |
| WO | WO-2004043381 A2 | 5/2004 |
| WO | WO-2004105837 A2 | 12/2004 |
| WO | WO-2006029233 A2 | 3/2006 |
| WO | WO-2006044790 A2 | 4/2006 |
| WO | WO-2006076401 A2 | 7/2006 |
| WO | WO-2008017121 A1 | 2/2008 |
| WO | WO-2008017123 A1 | 2/2008 |
| WO | WO-2008034476 A1 | 3/2008 |
| WO | WO-2010005959 A1 | 1/2010 |
| WO | WO-2010088364 A2 | 8/2010 |
| WO | WO-2011014855 A2 | 2/2011 |
| WO | WO-2011046841 A1 | 4/2011 |
| WO | WO-2011046963 A1 | 4/2011 |
| WO | WO-2012109107 A1 | 8/2012 |
| WO | WO-2012125955 A2 | 9/2012 |
| WO | WO-2012125955 A3 | 9/2012 |

OTHER PUBLICATIONS

"International Application Serial No. PCT/US2012/029510, International Search Report mailed Oct. 29, 2012", 3 pgs.

"International Application Serial No. PCT/US2012/029510, Written Opinion mailed Oct. 29, 2012", 4 pgs.

"Report of the US Department of Health and Human Services", The 2009 national blood collection and utilization survey report, ISBN 978-1-56395-328-6, (2009), 64 pgs.

"Standard for Blood Banks and Transfusion Services", 28th edition,, (Nov. 1, 2012), 122 pgs.

"The Future Use of Pathogen-inactivated platelet concentrates", Vox Sanguinis, vol. 85, International Forum, (2003), 54-66.

Aubuchon, James P., et al., "Further evaluation of a new standard of efficacy for stored platelets", Transfusion, vol. 45, (Jul. 2005), 1143-1150.

Aubuchon, James P., "Platelet Transfusion Therapy", Clinics in Laboratory Medicine, vol. 16, No. 4, (1996), 797-816.

Aubuchon, James P., et al., "Preliminary validation of a new standard of efficacy for stored platelets", Transfusion, vol. 44, (Jan. 2004), 36-41.

Bode, Arthur P., "Platelet activation may explain the storage lesion in platelet concentrates", Blood Cells, vol. 16, No. 1, discussion 125, (1990), 109-126.

Cartledge, S., et al., "Citrate metabolism by human platelets", Transfusion Medicine, vol. 7, (1997), 211-215.

Chace, Donald H, et al., "Factors affecting the loss of carbon monoxide from stored blood samples", Journal of Analytical Toxicology, vol. 10, No. 5, (1986), 181-189.

Collins, et al., "Acid-Base Status of Seriously Wounded Combat Casualties", Annals of Surgery, vol. 173(1), (Jan. 1971), 6-18.

Constantine, et al., "Rate of the reaction of carbon dioxide with human red blood cells", American Journal of Physiology, vol. 208, 801-811.

D'Agostino, Dominic P., et al., "Effects of hyperbaric gases on membrane nanostructure and function in neurons", Journal of Applied Physiology, vol. 106, (2009), 996-1003.

Daly, Peter A., et al., "Successful Transfusion of Platelets Cryopreserved for More Than 3 Years", Blood, vol. 54, No. 5, (Nov. 1979), 1023-1027.

De Mendona, et al., "Maintenance of 2,3-DPG and ATP levels in blood stored for 30 days at a constant pH obtained by variation of $CO_2$", vol. 35, (1978), 184-192.

Dean, Jay B., et al., "Neuronal sensitivity to hyperoxia, hypercapnia, and inert gases at hyperbaric pressures", J Appl. Physiol. vol. 95, (2003), 883-909.

(56) References Cited

OTHER PUBLICATIONS

Dumont, Larry J, et al., "Anaerobic Storage of Red Blood Cells in a Novel Additive Solution Improves in vivo Recovery", Transfusion 49(3), [Online]. Retrieved from the Internet <http://www.ncbi.nlm.nih.gov/pmc/articles/PMC2710818/pdf/nihms115451.pdf>, (Mar. 2009), 458-464.

Dumont, Larry J, et al., "Seven-Day Storage of Single-donor Platelets: Recovery and Survival in an Autologous Transfusion Study", Transfusion, vol. 42, (Jul. 2002), 847-854.

Eisele, John H., et al., "Narcotic Properties of Carbon dioxide in the dog", Anesthesiology, vol. 28, No. 5, (1967), 856-865.

Goodrich, Raymond P., et al., "The Mirasol TM PRT System for Pathogen reduction of Platelets and Plasma: An Overview of Current Status and Future Trends", Transfusion and Apheresis Science, vol. 35, (2006), 5-17.

Hamza, V. Zareena, et al., "A Simple Method to Irradiate Blood Cells In Vitro With Radon Gas", Radiation Protection Dosimetry, vol. 130, No. 3, (Mar. 4, 2008), 343-350.

Heaton, W.A.L., et al., "Development of a combined storage medium for 7-day storage of platelet concentrates and 42-day storage of red cell concentrates", British Journal of Haematology, vol. 75, No. 3, (1990), 400-407.

Hess, et al., "Storage of Red Blood Cells: New Approaches", Transfusion Medicine Reviews, vol. 16(4), (Oct. 2002), 283-295.

Hess, J.R., et al., "Interlaboratory comparison of red-cell ATP, 2,3-diphosphoglycerate and haemolysis measurements", Vox Sanguinis, vol. 89, (2005), 44-48.

Hirakawa, Senri, et al., "Transport of Na+ and HCO3- Out of Red Blood Cells Is Simultaneous with a Chloride Shift in Canine and Human Whole Blood Exposed to CO2-Rich Gas", Japanese Journal of Physiology, vol. 43, (1993), 35-49.

Holme, S., et al., "Concurrent label method with 111In and 51Cr allows accurate evaluation of platelet viability of stored platelet concentrates", British Journal of Haematology, vol. 84, Issue 4, (1993), 717-723.

Holme, S., et al., "Platelet storage lesion in second-generation containers_correlation with platelet ATP levels", Vox Sanguinis, vol. 53, No. 4, (1987), 214-220.

Holme, S., et al., "Platelet storage lesions in second-generation containers: correlation with the in vivo behavior with storage up to 14 days", Vox Sanguinis, vol. 59, No. 1, (1990), 12-18.

Holme, Stein, et al., "Platelet storage at 22 degrees C for transfusion interrelationship of platelet density and size, medium pH, and viability after in vivo infusion", Journal of Laboratory and Clinical Medicine, vol. 101, No. 1, (1983), 161-174.

Ishikawa, N., et al., "Effects of isosorbide dinitrate on thromboxane A2 synthesis in carbon dioxide exposed platelets", Arzneimittel-Forschung, vol. 38, No. 9, (1988), 1334-1335.

Jacobs, Michael R., et al., "Detection of bacterial contamination in prestorage culture-negative apheresis platelets on day of issue with the Pan Genera Detection test", Transfusion, vol. 51, (Dec. 2011), 2573-2582.

Kawamura, Kazunori, "Preservative Effects of Nitrous Oxide on Stored Red Cells", Department of Anesthesiology, Tottori University Hospital, vol. 46, No. 2, (1997), 222-228.

Kerry, P.J., et al., "Increased sensitivity of arachidonic acid-induced platelet aggregation in the presence of carbon dioxide", Br. J. Pharmac., vol. 81, (1984), 125-130.

Kilkson, H., et al., "Platelet metabolism during storage of platelet concentrates at 22 degrees C", Blood, vol. 64, No. 2, (Aug. 1984), 406-414.

Knutson, F., et al., "Pre-separation storage of whole blood: the effect of temperature on red cell 2,3-diphosphoglycerate and myeloperoxidase in plasma.", Transfusion Science, vol. 21, (1999), 111-115.

Koerner, K., "Platelet function of room temperature platelet concentrates stored in a new plastic material with high gas permeability", Vox Sanguinis, vol. 47 No. 6, (1984), 406-411.

Kotze, Harry F, et al., "Comparison of oxine and tropolone methods for labeling human platelets with Indium-111", The Journal of Nuclear Medicine vol. 32 No. 1, (Jan. 1991), 62-66.

Kouketsu, Keiko, et al., "Storage of Apheresis Platelets in Ethylene—Vinyl Acetate Copolymer Bags: Relationship between the Bag Size and the Number of Platelets Maintaining Aerobic Metabolism", Cryobiology, vol. 25, No. 5, (1988), 440-444.

Kurata, Yoshiyuki, et al., "New approach to eliminate HLA class I antigens from platelet surface without cell damage: acid treatement at pH 3.0.", Vox Sanguinis, vol. 57 No. 3, (1989), 199-204.

Leach, M.F., et al., "Effect of Storage Time on Clinical Efficacy of Single-Donor Platelet Units", Transfusion [0041-1132], vol. 33, No. 8, (1993), 661-664.

Mohr, Harald, et al., "Sterilization of Platelet Concentrates at Production Scale by Irradiation With Short-Wave Ultraviolet Light", Transfusion, vol. 49, (Sep. 2009), 1956-1963.

Moroff, Gary, et al., "Concepts About Current Conditions for the Preparation and Storage of Platelets", Transfusion Medicine Reviews, vol. V, No. 1, (Jan. 1991), 48-59.

Moroff, Gary, et al., "Factors influencing changes in pH during storage of platelet concentrates at 20-24 degree C", Vox Sang. vol. 42, (1982), 33-45.

Morrow, John F., et al., "Septic Reactions to Platelet Transfusions: A Persistent Problem", JAMA, vol. 266, No. 4, (Jul. 1991), 555-558.

Mulhausen, et al., "Effect of high CO2 tension on banked ACD blood", Metabolism, vol. 13(1), (Jan. 1964), 80-86.

Murphy, S, et al., "Platelet storage at 22 degrees C: role of gas transport across plastic containers in maintenance of viability", Blood, vol. 46, No. 2, (Aug. 1975), 209-218.

Murphy, Scott, "Platelet storage for transfusion", Seminars in hematology, vol. 22, No. 3, (1985), 165-177.

Philp, R.B., et al., "Effects of elevated pressures of inert gases on cytosolic free Ca2+ of human platelets stimulated with ADP", Cell Calcium, vol. 14, No. 7, (1993), 525-529.

Rao, G.H.R., et al., "Biochemistry, physiology and function of platelets stored as concentrates", Transfusion [0041-1132], vol. 33 Issue 9, (1993), 766-778.

Ridgway, R.L., et al., "Cryopreservation of platelets simplified: a modified glycerol-glucose method", Transfusion [0041-1132], vol. 20, No. 4, (1980), 427-432.

Rock, G., et al., "Platelet storage: an assessment of the requirements for plasma and oxygen", Transfusion, vol. 21, No. 2, (1981), 167-177.

Schmidt, C., et al., "Stability of pO2, pCO2 and pH in heparinized whole blood samples: influence of storage temperature with regard to leukocyte count and syringe material.", European Journal of Clinical Chemistry and Clinical Biochemistry, vol. 30, No. 11, (1992), 767-773.

Shimizu, Tetsuo, et al., "Dependence of the number of platelets maintaining aerobic metabolism on the size of storage containers", Tohoku Journal Exp. Med., vol. 156, (1988), 91-98.

Silva, Marianne A., et al., "Summary of the AABB Interorganizational Task Force on Bacterial Contamination of Platelets: Fall 2004 impact survey", Transfusion, vol. 46, (Apr. 2006), 636-641.

Skripchenko, Andrey, et al., "Mitochondrial dysfunction of platelets stored in first- and second-generation containers is, in part, associated with elevated carbot dioxide levels", Transfusion, vol. 51, (Feb. 2011), 371-379.

Snyder, Edward L., et al., "Occurrence of the release reaction during preparations and storage of platelet concentrates", Vox Sanguinis, vol. 41, No. 3, (1981), 172-177.

Tegos, C., et al., "Platelet glycolysis in platelet storage III. The inability of platelets to utilize exogenous citrate.", Transfusion, vol. 19, No. 5, (1979), 601-603.

Van Der Meer, Pieter F., et al., "Platelet preservation: Agitation and containers", Transfusion and Apheresis Science vol. 44, (2011), 297-304.

Vandenbroeke, T., et al., "Platelet storage solution affects on the accuracy of laboratory tests for platelet function a multi-laboratory study", Vox Sanguinis, vol. 86, (2004), 183-188.

Wagner, Stephen J., et al., "Evaluation of in vitro storage properties of prestorage pooled whole blood-derived platelets suspended in 100

(56) References Cited

OTHER PUBLICATIONS percent plasma and treated with amotosalen and long-wavelength ultraviolet light", Transfusion, vol. 49, (Apr. 2009), 704-710.

Wallvik, Jonas, et al., "Limited metabolic effect of mononuclear cells in platelet storage", Thrombosis Research, vol. 70, No. 3, (1993), 255-264.

Watts, S.E., et al., "Storage of Platelets for Tests of Platelet Function: Comparison of Two Methods of pH Control", Thrombosis Research, vol. 37, (1985), 73-83.

Yoshida, T., et al., "Extended storage of red blood cells under anaerobic conditions", Journal Compilation, Vox Sanguinis, vol. 92, (2007), 22-31.

Yoshida, Tatsuro, et al., "The effects of additive solution pH and metabolic rejuvenation on anaerobic storage of red cells.", Transfusion, vol. 48, (Oct. 2008), 2096-2105.

Zou, Yong, et al., "Acid treatment of platelets for removal of class I human leukocyte antigen (HLA) antigens", Scientific Research and Essays, vol. 6, No. 21, Available online at http://www.academicjournals.org/SRE, (Sep. 30, 2011), 4539-4544.

Chinese Application Serial No. 201280023194.6, Office Action mailed Sep. 12, 2014, 9 pgs.

European Application Serial No. 12757403.6, Extended European Search Report mailed Aug. 18, 2014, 5 pgs.

European Application Serial No. 12757403.6, Response filed Mar. 2, 2015 to Extended European Search Report mailed Aug. 18, 2014, 13 pgs.

Buchholz, D H, et al., "Extended storage of single-donor platelet concentrate collected by a blood cell separator", Transfusion, vol. 25, No. 6 (Nov. 1, 1985), 557-562.

\* cited by examiner

METHODS AND MATERIALS FOR PROLONGING USEFUL STORAGE OF RED BLOOD CELL PREPARATIONS AND PLATELET PREPARATIONS

CLAIM OF PRIORITY

This application is a continuation application of U.S. patent application Ser. No. 13/816,775, filed on Feb. 13, 2013, which claims the benefit of priority to a U.S. National Stage Filing under 35 U.S.C. 371 from International Application No. PCT/US2012/029510, filed on Mar. 16, 2012 and published as WO 2012/125955 A1 on Sep. 20, 2012, which claims the benefit of priority of U.S. Provisional Patent Application Ser. No. 61/453,455, filed Mar. 16, 2011; and U.S. Provisional Patent Application Ser. No. 61/562,331, filed Nov. 21, 2011, which applications and publication are incorporated by reference herein in their entirety.

BACKGROUND

1. Technical Field

This document relates to methods and materials involved in prolonging useful storage of red blood cell preparations. For example, this document relates to methods and materials for storing red blood cells in a manner that reduces the level of glucose or 2,3-diphosphoglycerate (2,3-DPG) consumption of or reduces the level of 2,3 DPG production by a red blood cell preparation, that reduces the level of lactate formation by a red blood cell preparation, and/or that reduces the pH level of a red blood cell preparation, thereby prolonging the useful lifespan of the red blood cells of the red blood cell preparation. This document also relates to methods and materials involved in prolonging useful storage of platelet preparations. For example, this document relates to methods and materials for storing platelets in a manner that reduces platelet metabolism, that preserves platelet function, and/or that reduces the risk of bacterial contamination, thereby prolonging the useful lifespan of the platelets of a platelet preparation.

2. Background Information

In general, red blood cells can be stored for about 42 days in blood banks During this time, a so-called storage lesion can occur, thereby limiting the ability of the surviving red blood cells to carry oxygen. Storage lesions are thought to result from anaerobic glycolysis, depleted energy stores in the cells, a reduction in 2-3 DPG, and other adverse metabolic events including oxidative stress.

There is an increase in demand for platelet transfusions in clinical medicine. Meeting the demand for platelets is challenging because they can have a limited shelf life. The short shelf life also makes the efficient collection, processing, and distribution of platelets challenging.

SUMMARY

This document provides methods and materials for enhancing the storage capabilities of red blood cell preparations. For example, this document provides methods and materials for using $CO_2$ to store red blood cells in a manner that (a) reduces the level of glucose or 2,3-DPG consumption of or reduces the level of 2,3 DPG production by a red blood cell preparation, (b) reduces the level of lactate formation by a red blood cell preparation, and/or (c) reduces the pH level of a red blood cell preparation. Such methods and materials can result in prolonging the useful lifespan of the red blood cells of the red blood cell preparation.

In general, storage of red blood cells (RBCs) at 4° C. can result in an increase in the oxygen affinity of the RBC hemoglobin (Hb), which can have negative consequences for the delivery of oxygen to tissue after transfusion. During storage of RBCs, large amounts of lactate can be formed, and blood pH can drop rapidly. Because glycolysis is temperature-dependent and pH-dependent, the more time passes between collection and refrigeration, the more rapid the reduction in pH will be. 2,3-DPG levels also can drop quickly when stored at room temperature. When the pH falls below about 7.2 (e.g., below 7.2 to 7.3), the bisphosphoglycerate phosphatase will be activated, and the normally high concentration of 2,3-DPG is rapidly depleted.

As described herein, red blood cells stored in an environment (e.g., a bag) containing $CO_2$ (e.g., greater than about 100 mmHg of $pCO_2$, greater than about 200 mmHg of $pCO_2$, greater than about 300 mmHg of $pCO_2$, greater than about 400 mmHg of $pCO_2$, or greater than about 500 mmHg of $pCO_2$) can exhibit reduced glucose consumption, reduced lactate formation, and lower pH levels than red blood cells stored under normal environmental air conditions (e.g., air having about 21 percent $O_2$ and about 40 to 60 mmHg of $pCO_2$). The drop in pH can occur as soon as the blood is exposed to $CO_2$, but this drop in pH is reversible. In general, it is not favorable to drop pH below 6.3, but the methods and materials provided here can be used to reduce pH in a manner that is reversible. In some cases, 100 percent $CO_2$, a mixture of $CO_2$ and Nitrogen (e.g., 50/50 $CO_2$—N), or a mixture of $CO_2$ and air (e.g., 50/50 $CO_2$-air) can be used as described herein, for example, to lower pH levels.

Red blood cells exposed to $CO_2$ and exhibiting reduced glucose consumption, reduced lactate formation, and lower pH levels (e.g., rapidly reversible lower pH levels) can have a longer useful lifespan than red blood cells not exhibiting reduced glucose consumption, reduced lactate formation, and lower pH levels. In some cases, the lower pH levels observed for red blood cells stored under conditions of greater than about 100 mmHg of $pCO_2$ (e.g., pH levels less than about 6.6, less than about 6.5, less than about 6.4, less than about 6.3, or less than about 6.2) can be reversible such that red blood cells switched from $CO_2$ conditions of greater than about 100 mmHg of $pCO_2$ to normal air conditions (e.g., about 21 percent $O_2$ and about 40 to 60 mmHg of $pCO_2$) can exhibit pH levels greater than about 6.6 (e.g., greater than about 6.7, greater than about 6.8, greater than about 6.9, or greater than about 7.0).

This document also provides methods and materials for enhancing the storage capabilities of platelet preparations. For example, this document provides methods and materials for using $CO_2$ to store platelets in a manner that (a) reduces platelet metabolism, (b) preserves platelet function, and/or (c) reduces the risk of bacterial contamination. Such methods and materials can result in prolonging the useful lifespan of the platelets of a platelet preparation.

Since platelets stored at temperatures from about 2° C. to about 6° C. typically form platelet aggregates, platelets are generally stored in high glucose media and at room temperature to reduce formation of platelet aggregates. Platelets stored in high glucose media and at room temperature, however, can deteriorate over time and have an increased risk of undergoing bacterial contamination. As described herein, a platelet preparation stored in an environment (e.g., a bag) containing $CO_2$ (e.g., greater than about 100 mmHg of $pCO_2$, greater than about 200 mmHg of $pCO_2$, greater than about 300 mmHg of $pCO_2$, greater than about 400 mmHg of $pCO_2$, or greater than about 500 mmHg of $pCO_2$) can exhibit reduced platelet metabolism, preserved platelet function, and reduced bacterial growth when compared to platelet preparations stored under normal environmental air conditions (e.g., air having about 21 percent $O_2$ and about 40 to 60 mmHg of $pCO_2$). In some cases, a platelet preparation stored in an environment (e.g., a bag) containing $CO_2$ (e.g., greater than about 100 mmHg of $pCO_2$, greater than about 200 mmHg of $pCO_2$, greater than about 300 mmHg of $pCO_2$, greater than about 400 mmHg of $pCO_2$, or greater than about 500 mmHg of $pCO_2$) can be stored at a temperature from about 2° C. to about 6° C. without forming a significant amount or a detectable amount of platelet aggregates.

In some cases, a drop in pH can occur as soon as a platelet preparation is exposed to $CO_2$, but this drop in pH can be reversible. In general, it is not favorable to drop pH below 6.0, but the methods and materials provided herein can be used to reduce pH in a manner that is reversible.

In some cases, a blood or platelet container (e.g., a blood collection bag or a platelet collection bag) provided herein can include an entry port for inserting blood or platelets into the blood or platelet container and a capsule positioned in a manner to deliver $CO_2$ material to the inner region of the blood or platelet container. For example, a blood or platelet container provided herein can include a breakable capsule located within the inner region of the blood or platelet container. The breakable capsule can house any type of material designed to deliver $CO_2$ gas to the inner region of the blood or platelet container. For example, the capsule can house $CO_2$ gas or a powder that produces $CO_2$ gas (e.g., bicarbonate). Before or after adding a red blood cell preparation (e.g., blood) to the blood container or before or after adding a platelet preparation to a platelet container, the capsule can be pierced or broken to release $CO_2$ gas into the inner region of the blood container or platelet container.

In some cases, a blood container (e.g., blood collection bag) provided herein can include an entry port for inserting blood into the blood container and can be connected to one or more satellite containers (e.g., a satellite bag) designed to house $CO_2$ gas or material capable of generating $CO_2$ gas. Before or after adding a red blood cell preparation (e.g., blood) to the blood container, a satellite container can be manipulated to move $CO_2$ gas into the blood container, thereby allowing $CO_2$ to contact the red blood cell preparation to be stored.

In some cases, a blood container (e.g., blood collection bag) provided herein can include an entry port for inserting blood into the blood container and an injection port configured to allow sterile $CO_2$ gas or material capable of generating $CO_2$ gas to be injected into the blood container. Before or after adding a red blood cell preparation (e.g., blood) to the blood container, sterile $CO_2$ gas or material capable of generating $CO_2$ gas can be injected into the blood container, thereby allowing $CO_2$ to contact the red blood cell preparation to be stored.

In some cases, a platelet container (e.g., platelet collection bag) provided herein can include an entry port for inserting platelets into the platelet container and can be connected to one or more satellite containers (e.g., a satellite bag) designed to house $CO_2$ gas or material capable of generating $CO_2$ gas. Before or after adding a platelet preparation (e.g., platelets) to the platelet container, a satellite container can be manipulated to move $CO_2$ gas into the platelet container, thereby allowing $CO_2$ to contact the platelet preparation to be stored.

In some cases, a platelet container (e.g., platelet collection bag) provided herein can include an entry port for inserting platelets into the platelet container and an injection port configured to allow sterile $CO_2$ gas or material capable of generating $CO_2$ gas to be injected into the platelet container. Before or after adding a platelet preparation (e.g., platelets) to the platelet container, sterile $CO_2$ gas or material capable of generating $CO_2$ gas can be injected into the platelet container, thereby allowing $CO_2$ to contact the platelet preparation to be stored.

In some cases, a platelet bag can be exposed to $CO_2$ in a $CO_2$ rich chamber, such as a bag within a bag. In such cases, the pH of the platelet preparation can drop to about 6.2 in about 10 minutes when, for example, commercially available platelet storage bags that have olefins within the plasticizer (e.g., Fenwal PL732 gas permable bags) are used to allow for gas exchange.

In general, one aspect of this document features a method for reducing the rate of lactate formation or glucose consumption by stored red blood cells of a red blood cell preparation. The method comprises, or consists essentially of, exposing the red blood cell preparation to $CO_2$ gas under conditions wherein the $pCO_2$ level of the red blood cell preparation is greater than 100 mmHg of $pCO_2$. The method can comprise exposing the red blood cell preparation to $CO_2$ gas under conditions wherein the $pCO_2$ level of the red blood cell preparation is greater than 200 mmHg of $pCO_2$. The method can comprise exposing the red blood cell preparation to $CO_2$ gas under conditions wherein the $pCO_2$ level of the red blood cell preparation is greater than 300 mmHg of $pCO_2$. The method can comprise exposing the red blood cell preparation to $CO_2$ gas under conditions wherein the $pCO_2$ level of the red blood cell preparation is greater than 400 mmHg of $pCO_2$. The method can comprise exposing the red blood cell preparation to $CO_2$ gas under conditions wherein the $pCO_2$ level of the red blood cell preparation is greater than 500 mmHg of $pCO_2$. The method can comprise exposing the red blood cell preparation to $CO_2$ gas under conditions wherein the $pCO_2$ level of the red blood cell preparation is between 200 and 600 mmHg of $pCO_2$. The method can comprise exposing the red blood cell preparation to $CO_2$ gas under conditions wherein the $pCO_2$ level of the red blood cell preparation is between 450 and 550 mmHg of $pCO_2$. The method can comprise reducing the rate of lactate formation to a level that results in less than 7.5 μmol/mL of lactate being formed after 14 days of storage. The method can comprise reducing the rate of lactate formation to a level that results in less than 10 μmol/mL of lactate being formed after 21 days of storage. The method can comprise reducing the rate of glucose consumption to a level that results in greater than 450 mg/dL of glucose being present after 14 days of storage. The method can comprise reducing the rate of glucose consumption to a level that results in greater than 200 mg/dL of glucose being present after 21 days of storage. The method can comprise reducing the rate of glucose consumption to a level that results in greater than 300 mg/dL of glucose being present after 21 days of storage. The method can comprise reducing the rate of glucose consumption to a level that results in greater than 400 mg/dL of glucose being present after 21 days of storage. The pH of the red blood cell preparation can be less than 6.8 after 14 days of storage. The pH of the red blood cell preparation can be less than 6.6 after 14 days of storage. The pH of the red blood cell preparation can be less than 6.4 after 14 days of storage. The pH of the red blood cell preparation can be less than 6.6 after 21 days of storage. The pH of the red blood cell preparation can be less than 6.4 after 21 days of storage.

In another aspect, this document features a method for reducing the rate of lactate formation or glucose consumption by stored red blood cells of a red blood cell preparation, wherein the method comprises, or consists essentially of, exposing the red blood cell preparation to $CO_2$ gas under conditions wherein the pH of the red blood cell preparation is less than 6.6. The method can comprise exposing the red blood cell preparation to $CO_2$ gas under conditions wherein the pH of the red blood cell preparation is less than 6.4. The method can comprise exposing the red blood cell preparation to $CO_2$ gas under conditions wherein the pH of the red blood cell preparation is less than 6.3. The $pCO_2$ of the red blood cell preparation can be greater than 100 mmHg of $pCO_2$. The $pCO_2$ of the red blood cell preparation can be greater than 200 mmHg of $pCO_2$. The $pCO_2$ of the red blood cell preparation can be greater than 300 mmHg of $pCO_2$. The $pCO_2$ of the red blood cell preparation can be greater than 400 mmHg of $pCO_2$. The $pCO_2$ of the red blood cell preparation can be greater than 500 mmHg of $pCO_2$. The $pCO_2$ of the red blood cell preparation can be between 200 and 600 mmHg of $pCO_2$. The $pCO_2$ of the red blood cell preparation can be between 450 and 550 mmHg of $pCO_2$. The method can comprise reducing the rate of lactate formation to a level that results in less than 7.5 μmol/mL of lactate being formed after 14 days of storage. The method can comprise reducing the rate of lactate formation to a level that results in less than 10 μmol/mL of lactate being formed after 21 days of storage. The method can comprise reducing the rate of glucose consumption to a level that results in greater than 450 mg/dL of glucose being present after 14 days of storage. The method can comprise reducing the rate of glucose consumption to a level that results in greater than 200 mg/dL of glucose being present after 21 days of storage. The method can comprise reducing the rate of glucose consumption to a level that results in greater than 300 mg/dL of glucose being present after 21 days of storage. The method can comprise reducing the rate of glucose consumption to a level that results in greater than 400 mg/dL of glucose being present after 21 days of storage.

In another aspect, this document features a blood container comprising, or consisting essentially of, an inlet port configured to allow blood to be inserted into the blood container and a capsule comprising $CO_2$ gas or material capable of generating $CO_2$ gas, wherein the capsule is located in a position that allows the $CO_2$ gas or the material to be delivered to an inner region of the container. The capsule can be located within the inner region of the container. The capsule can comprise $CO_2$ gas. The capsule can comprise material capable of generating $CO_2$ gas. The material can be a bicarbonate salt. The blood container can comprise an exhaust valve configured to allow gas to be removed from the inner region of the blood container.

In another aspect, this document features a blood container system comprising, or consisting essentially of, a blood container having an inlet port configured to allow blood to be inserted into the blood container and a satellite container comprising $CO_2$ gas or material capable of generating $CO_2$ gas, wherein the satellite container is configured to be in fluid communication with an inner region of the blood container. The system can comprise a valve configured to retain the $CO_2$ gas or material within the satellite container. The valve can be capable of being opened to allow the $CO_2$ gas or material to exit the satellite container into the inner region of the blood container. The system can comprise a membrane configured to retain the $CO_2$ gas or material within the satellite container. The membrane can be capable of being broken to allow the $CO_2$ gas or material to exit the satellite container into the inner region of the blood container. The blood container can comprise an exhaust valve configured to allow gas to be removed from the inner region of the blood container.

In another aspect, this document features a blood container comprising, or consisting essentially of, an inlet port configured to allow blood to be inserted into the blood container and an injection port configured to allow sterile insertion of a needle for delivering $CO_2$ gas or material capable of generating $CO_2$ gas into an inner region of the container. The blood container can comprise an exhaust valve configured to allow gas to be removed from the inner region of the blood container.

In another aspect, this document features a platelet container comprising, or consisting essentially of, an inlet port configured to allow platelets to be inserted into the platelet container and a capsule comprising $CO_2$ gas or material capable of generating $CO_2$ gas, wherein the capsule is located in a position that allows the $CO_2$ gas or the material to be delivered to an inner region of the container.

In another aspect, this document features a platelet container system comprising, or consisting essentially of, a platelet container having an inlet port configured to allow platelets to be inserted into the platelet container and a satellite container comprising $CO_2$ gas or material capable of generating $CO_2$ gas, wherein the satellite container is configured to be in fluid communication with an inner region of the platelet container.

In another aspect, this document features a platelet container comprising, or consisting essentially of, an inlet port configured to allow platelets to be inserted into the platelet container and an injection port configured to allow sterile insertion of a needle for delivering $CO_2$ gas or material capable of generating $CO_2$ gas into an inner region of the container.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
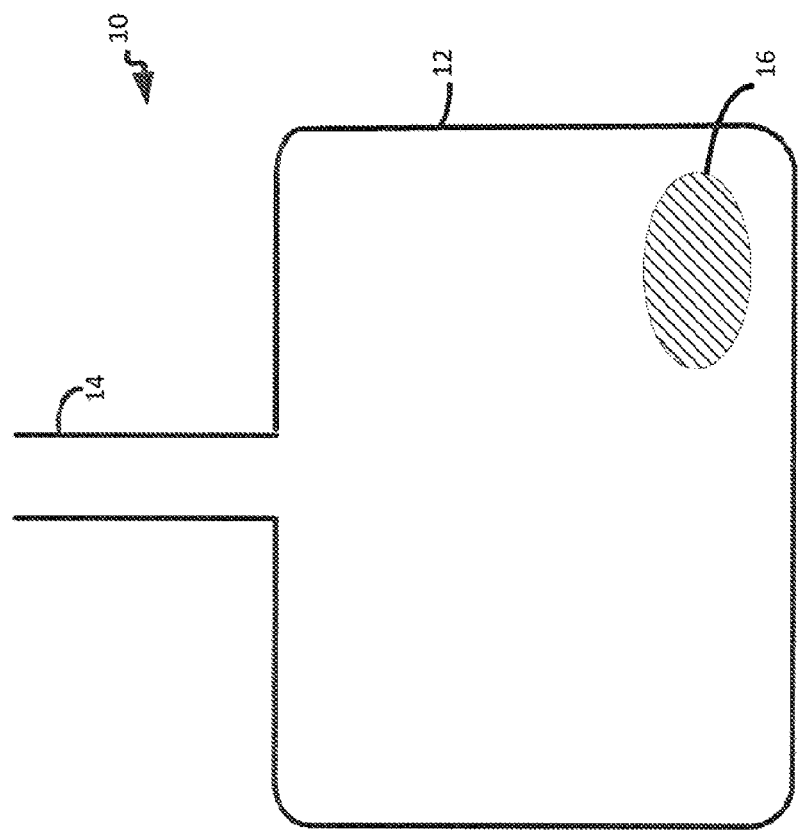
FIG. 1 is a front view of one example of a blood container device containing a capsule having $CO_2$ gas or material capable of generating $CO_2$ gas.

This document provides methods and materials for enhancing the storage capabilities of red blood cell preparations. For example, this document provides methods and materials for using $CO_2$ to store red blood cells in a manner that (a) reduces the level of glucose or 2,3-DPG consumption of or reduces the level of 2,3 DPG production by a red blood cell preparation, (b) reduces the level of lactate formation by a red blood cell preparation, and/or (c) reduces the pH level of a red blood cell preparation. Such methods and materials can result in prolonging the useful lifespan of the red blood cells of the red blood cell preparation.

As described herein, red blood cell preparations can be stored in an environment (e.g., a bag) containing $CO_2$ or can be exposed to $CO_2$ such that the level of $pCO_2$ of the preparation is greater than about 100 mmHg of $pCO_2$ (e.g., greater than about 150 mmHg of $pCO_2$, greater than about 200 mmHg of $pCO_2$, greater than about 300 mmHg of $pCO_2$, greater than about 400 mmHg of $pCO_2$, or greater than about 500 mmHg of $pCO_2$). In some cases, red blood cell preparations can be stored in an environment containing $CO_2$ or can be exposed to $CO_2$ such that the level of $pCO_2$ of the preparation is between about 100 mmHg of $CO_2$ and about 600 mmHg of $pCO_2$ (e.g., between about 150 mmHg of $CO_2$ and about 600 mmHg of $pCO_2$, between about 200 mmHg of $CO_2$ and about 600 mmHg of $pCO_2$, between about 200 mmHg of $CO_2$ and about 550 mmHg of $pCO_2$, or between about 450 mmHg of $CO_2$ and about 550 mmHg of $pCO_2$). In some cases, a minimum volume of $CO_2$ required to raise the $pCO_2$ of a 300 mL bag containing a red blood cell preparation to 400 mm Hg can be used. For example, 2, 3, 4, 5, 6, 7, 8, 9, 10, or more cubic centimeters of $CO_2$ can be used.

Any appropriate method can be used to expose a red blood cell preparation to $CO_2$. For example, $CO_2$ gas or material capable of generating $CO_2$ gas can be placed into a container designed to house a red blood cell preparation prior to adding the red blood cell preparation. Examples of materials capable of generating $CO_2$ gas include, without limitation, bicarbonate, bicarbonate salts, and bismuth subsalicylate. In some cases, $CO_2$ gas or material capable of generating $CO_2$ gas can be added to container already containing a red blood cell preparation. In some cases, excess gas can be removed from a container containing a red blood cell preparation exposed to $CO_2$ gas.

In some cases, a container that is not $CO_2$ permeable can be used to store a red blood cell preparation. For example, blood bags and glass containers can be used to store red blood cell preparations in a manner that maintains high $CO_2$ levels for at least 30, 40, 41, 42, 43, 45, 50, 55, or 60 days.

This document also provides methods and materials for enhancing the storage capabilities of platelet preparations. For example, this document provides methods and materials for using $CO_2$ to store platelets in a manner that (a) reduces platelet metabolism, (b) preserves platelet function, and/or (c) reduces the risk of bacterial contamination. Such methods and materials can result in prolonging the useful lifespan of the platelets of a platelet preparation.

As described herein, platelet preparations can be stored in an environment (e.g., a bag) containing $CO_2$ or can be exposed to $CO_2$ such that the level of $pCO_2$ of the preparation is greater than about 100 mmHg of $pCO_2$ (e.g., greater than about 150 mmHg of $pCO_2$, greater than about 200 mmHg of $pCO_2$, greater than about 300 mmHg of $pCO_2$, greater than about 400 mmHg of $pCO_2$, or greater than about 500 mmHg of $pCO_2$). In some cases, platelet preparations can be stored in an environment containing $CO_2$ or can be exposed to $CO_2$ such that the level of $pCO_2$ of the preparation is between about 100 mmHg of $CO_2$ and about 600 mmHg of $pCO_2$ (e.g., between about 150 mmHg of $CO_2$ and about 600 mmHg of $pCO_2$, between about 200 mmHg of $CO_2$ and about 600 mmHg of $pCO_2$, between about 200 mmHg of $CO_2$ and about 550 mmHg of $pCO_2$, or between about 450 mmHg of $CO_2$ and about 550 mmHg of $pCO_2$). In some cases, a minimum volume of $CO_2$ required to raise the $pCO_2$ of a 300 mL bag containing a platelet preparation to 400 mm Hg can be used. For example, 2, 3, 4, 5, 6, 7, 8, 9, 10, or more cubic centimeters of $CO_2$ can be used.

Any appropriate method can be used to expose a platelet preparation to $CO_2$. For example, $CO_2$ gas or material capable of generating $CO_2$ gas can be placed into a container designed to house a platelet preparation prior to adding the platelet preparation. Examples of materials capable of generating $CO_2$ gas include, without limitation, bicarbonate and bicarbonate salts. In some cases, $CO_2$ gas or material capable of generating $CO_2$ gas can be added to container already containing a platelet preparation. In some cases, excess gas can be removed from a container containing a platelet preparation exposed to $CO_2$ gas.

In some cases, a container that is not $CO_2$ permeable can be used to store a platelet preparation. For example, platelet bags and glass containers can be used to store platelet preparations in a manner that maintains high $CO_2$ levels for an appropriate period of time (e.g., until the product is released for transfusion). In another example, rigid PET bottles or glass bottles that do not have $CO_2$ exchange can be used. In some cases, at the time of release, a quick and easy de-gas step can be performed.

With reference to FIG. 1, blood container device 10 can include a blood container component 12 and an inlet port 14 configured to allow a red blood cell preparation to be inserted into blood container component 12. Blood container device 10 can include a capsule 16 within blood container component 12. Capsule 16 can contain $CO_2$ gas or material capable of generating $CO_2$ gas. In some cases, capsule 16 can be breakable such that a user can break capsule 16 (e.g., by squeezing) at a desired time point to release its contents (e.g., $CO_2$ gas or material capable of generating $CO_2$ gas).

Figure 2:
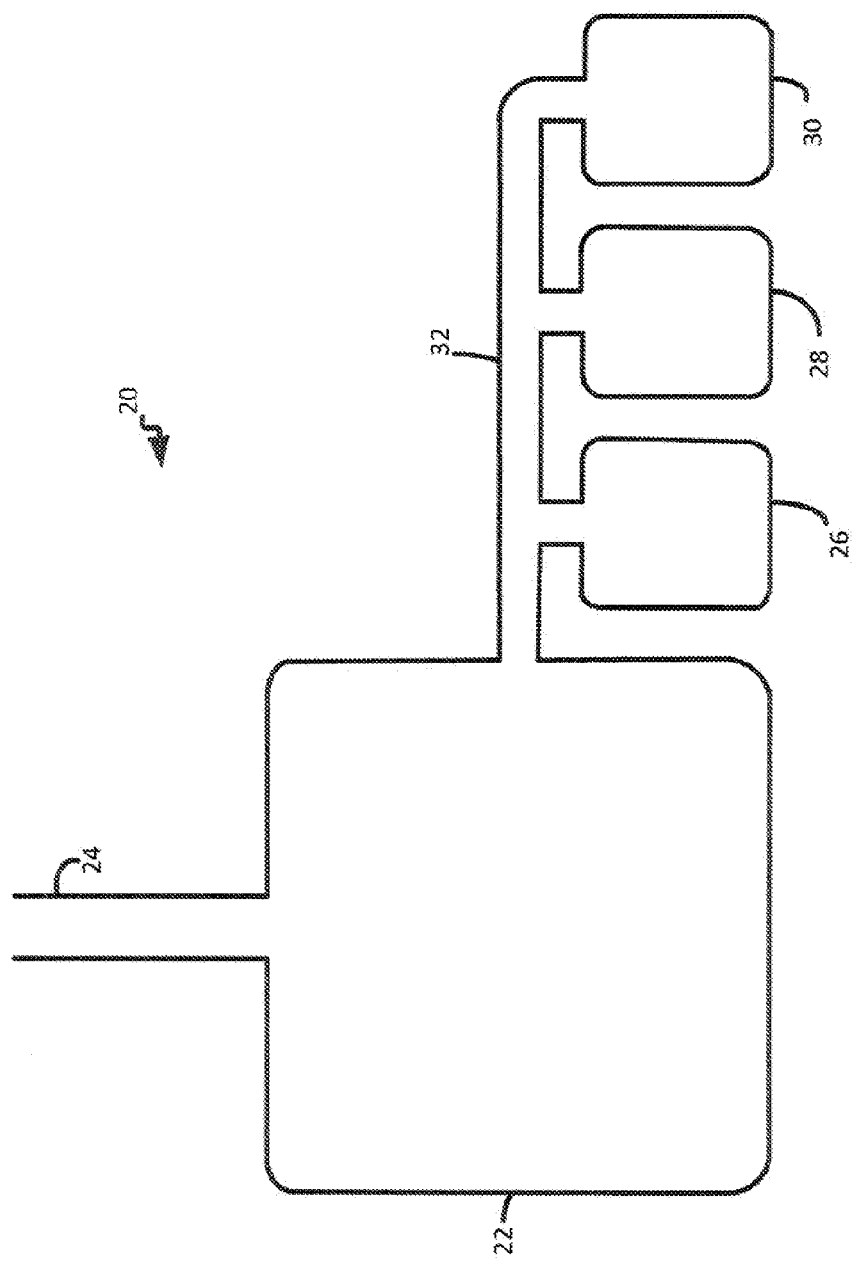
FIG. 2 is a front view of an exemplary blood container system including a blood container device fluidly attached to multiple satellite containers.

With reference to FIG. 2, blood container system 20 can include a blood container component 22 and an inlet port 24 configured to allow a red blood cell preparation to be inserted into blood container component 22. Blood container system 20 can include one or more satellite containers such as satellite containers 26, 28, and 30. Satellite containers 26, 28, and 30 can be fluidly connected to an inner region of blood container component 22 via a channel 32 (e.g., a tube). In some cases, satellite containers 26, 28, and 30 can be fluidly connected to each other. One or more of the satellite containers can contain $CO_2$ gas or material capable of generating $CO_2$ gas. For example, satellite container 30 can contain $CO_2$ gas or material capable of generating $CO_2$ gas. In some cases, blood container system 20 can include a valve or membrane configured to retain $CO_2$ gas or material capable of generating $CO_2$ gas within a satellite container until a user decides to allow the $CO_2$ gas or material capable of generating $CO_2$ gas to be released and moved into an inner region of blood container component 22.

In some cases, a satellite container can be designed to house blood components such as platelets or plasma. For example, satellite container 26 can be designed to house platelets, and satellite container 28 can be designed to house plasma.

Figure 3:
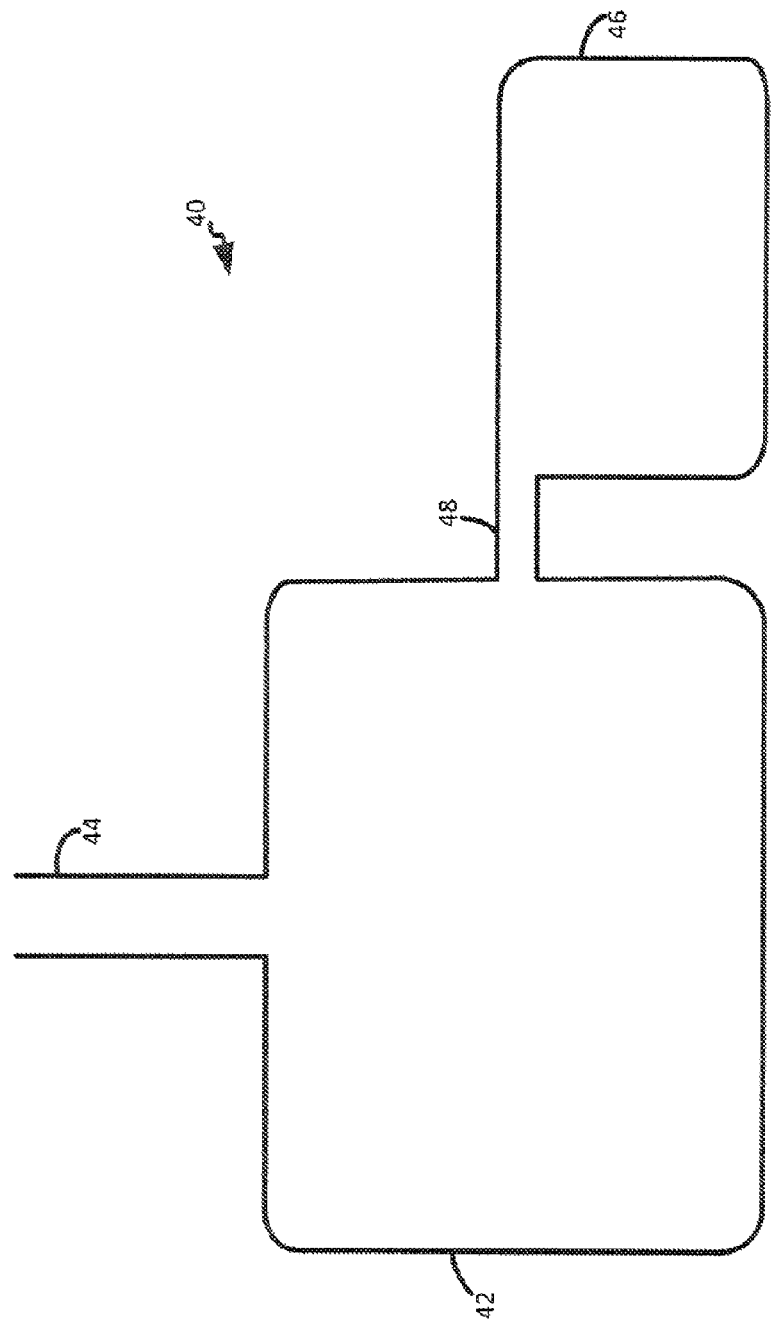
FIG. 3 is a front view of an exemplary blood container system including a blood container device fluidly attached to one satellite container.

With reference to FIG. 3, blood container system 40 can include a blood container component 42 and an inlet port 44 configured to allow a red blood cell preparation to be inserted into blood container component 42. Blood container system 40 can include one satellite container (e.g., satellite container 46). Satellite container 46 can be fluidly connected to an inner region of blood container component 42 via a channel 48 (e.g., a tube). Satellite container 46 can contain $CO_2$ gas or material capable of generating $CO_2$ gas. In some cases, blood container system 40 can include a valve or membrane configured to retain $CO_2$ gas or material capable of generating $CO_2$ gas within satellite container 46 until a user decides to allow the $CO_2$ gas or material capable of generating $CO_2$ gas to be released and moved into an inner region of blood container component 42.

Figure 4:
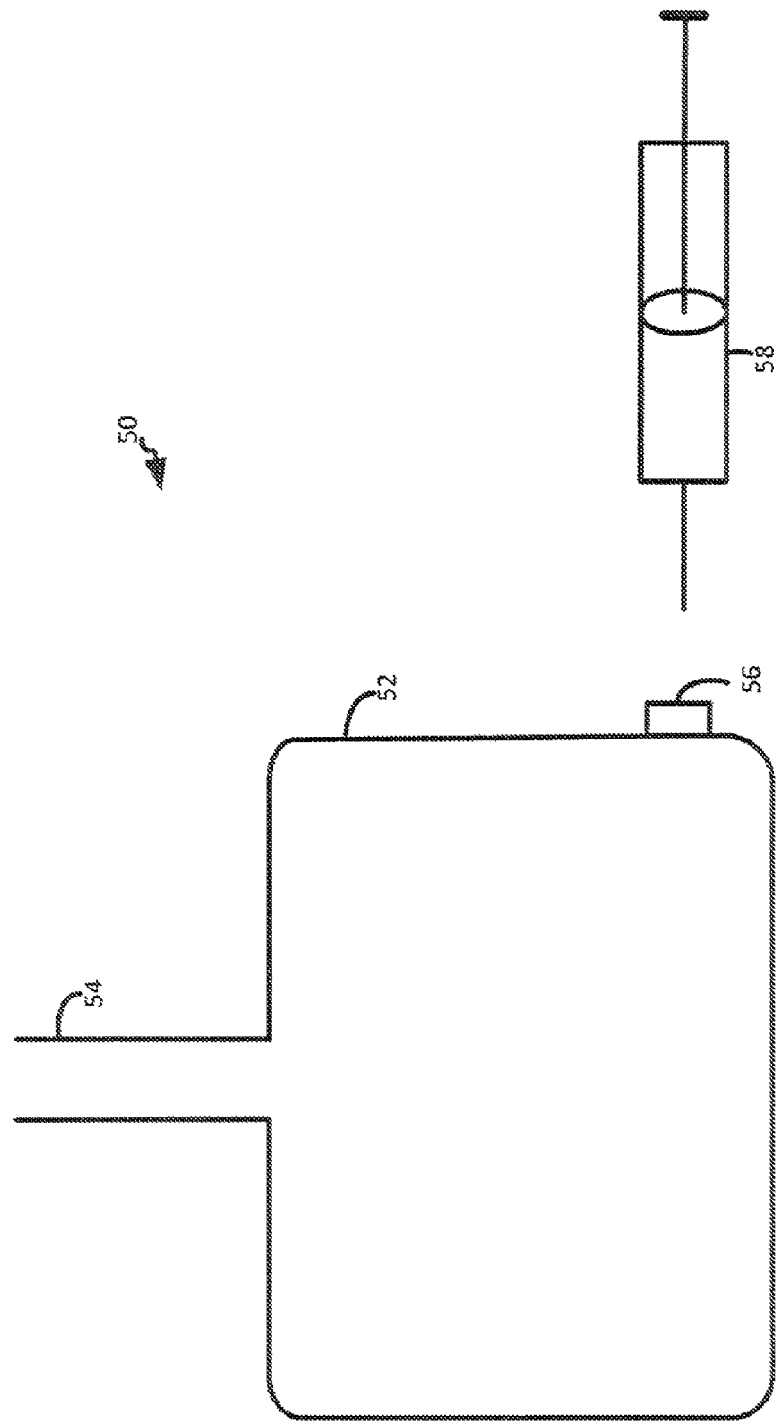
FIG. 4 is a front view of one example of a blood container device having an injection port for sterilely injecting $CO_2$ gas or material capable of generating $CO_2$ gas into an inner region of the blood container device.

In some cases, a blood container component provided herein can include an injection port. For example, with reference to FIG. 4, a blood container device 50 can include a blood container component 52 and an inlet port 54 configured to allow a red blood cell preparation to be inserted into blood container component 52. Blood container device 50 can include an injection port 56. Injection port 56 can be configured to allow a needle (e.g., of a syringe 58) to be inserted into an inner region of blood container component 52. The syringe can be used to deliver $CO_2$ gas or material capable of generating $CO_2$ gas into an inner region of blood container component 52 in a sterile manner. In some cases, injection port 56 can be configured to seal upon removal of an inserted needle.

Figure 5:
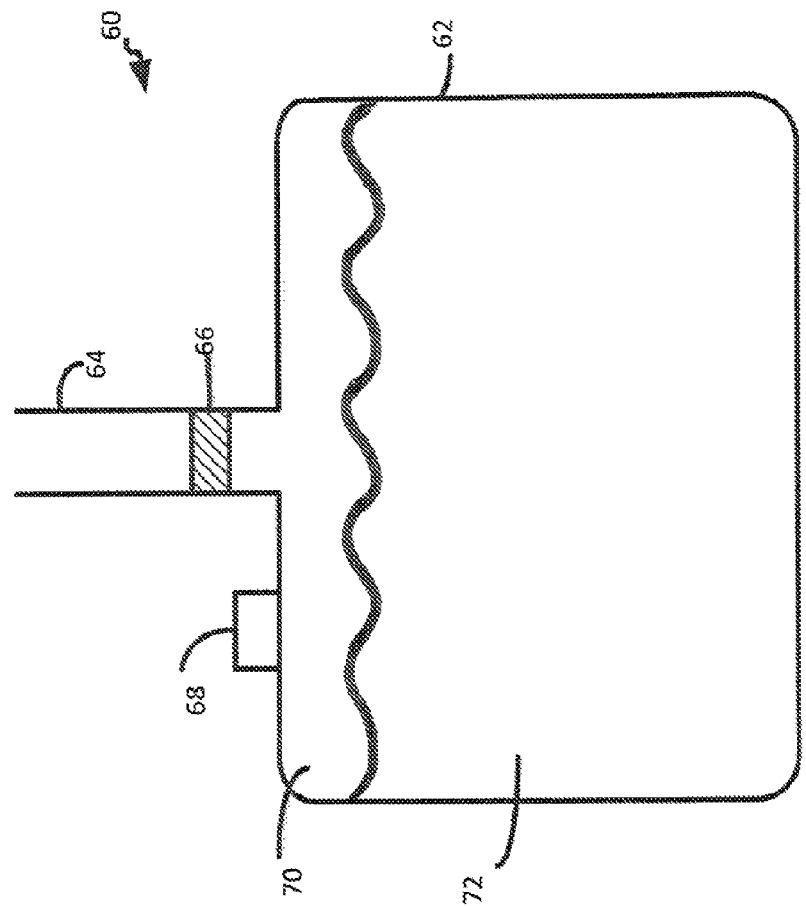
FIG. 5 is a front view of an exemplary blood container device having an exhaust port for allowing gas to be removed from the inner region of the blood container device.

In some cases, a blood container component provided herein can include an exhaust valve. For example, with reference to FIG. 5, a blood container device 60 can include a blood container component 62 and an inlet port 64 configured to allow a red blood cell preparation 72 to be inserted into blood container component 62. Blood container device 60 can include an exhaust valve 68. Exhaust valve 68 can be configured to allow a user to remove gas 70 present within an inner region of blood container component 62 in a sterile and sealable manner.

In some cases, a blood container component provided herein can include an inlet port 64 having a valve. For example, with reference to FIG. 5, inlet port 64 can be configured to have valve 66. Valve 66 can be configured to have open and closed configurations. When in an open configuration, valve 66 can allow fluids and gases to pass into and out of an inner region of blood container component 62. When in a closed configuration, valve 66 can prevent the contents within an inner region of blood container component 62 from exiting that region via inlet port 64.

In some cases, a blood bag can include a series of bags to facilitate the separation of blood into components. The blood can be first collected as whole blood (e.g., typically around 500 cubic centimeters) in a large bag, and other bags can receive the separated products during processing. In some cases, one of the bags not used in the initial collection of whole blood can be loaded with $CO_2$ for subsequent evacuation and mixing with the red blood cells. In some cases, a relatively small amount (e.g., 50-100 cubic centimeters) of $CO_2$ can be used to saturate the red blood cells completely.

In some cases, a bubble-like wrap-like reservoir with $CO_2$ can be incorporated into the blood bag, and a simple one-way valve can be configured to permit evacuation of $CO_2$ with gentle squeezing into the remaining red blood cells. In some cases, a sterile one-way valve can be used to permit the rapid dosing of $CO_2$ from a traditional gas tank or other source. This can be configured in a manner that injects a known amount of $CO_2$ in the bag. Due to the nature of gas in closed spaces and equilibration characteristics of $CO_2$ and blood, minimal mixing may be needed. In some cases, dry ice or another chemical reservoir that includes a phase change from solid to gas can be placed in the blood bag to liberate $CO_2$.

Figure 6:
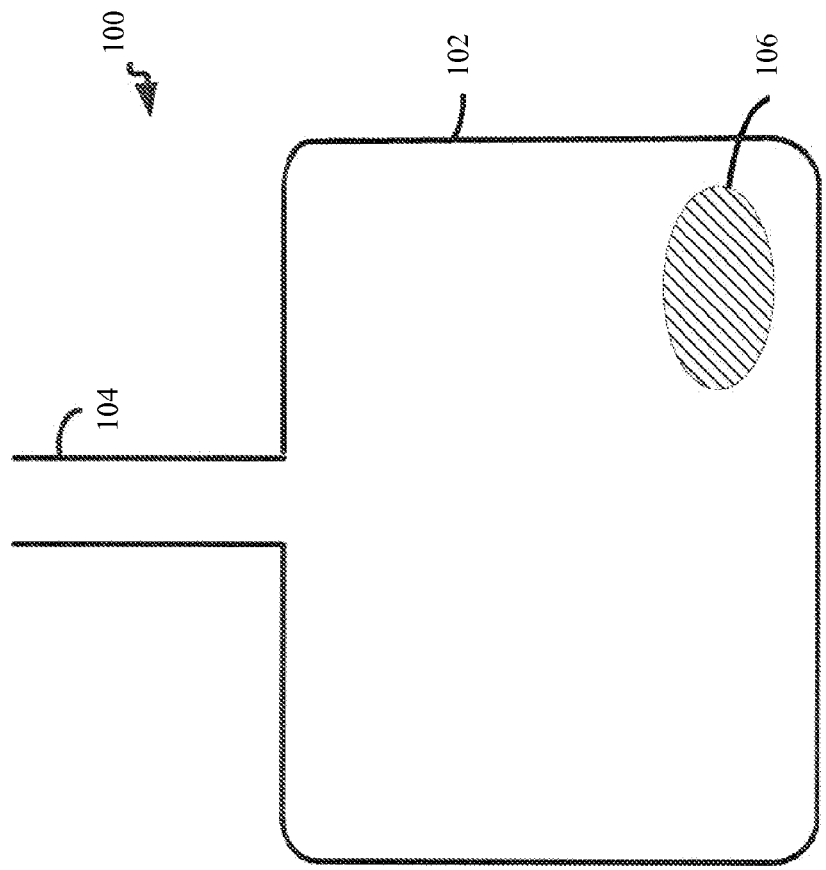
FIG. 6 is a front view of one example of a platelet container device containing a capsule having $CO_2$ gas or material capable of generating $CO_2$ gas.

In some cases, a platelet container device similar to a blood container device provided herein can be used to house a platelet preparation. With reference to FIG. 6, platelet container device 100 can include a platelet container component 102 and an inlet port 104 configured to allow a platelet preparation to be inserted into platelet container component 102. Platelet container device 100 can include a capsule 106 within platelet container component 102. Capsule 106 can contain $CO_2$ gas or material capable of generating $CO_2$ gas. In some cases, capsule 106 can be breakable such that a user can break capsule 106 (e.g., by squeezing) at a desired time point to release its contents (e.g., $CO_2$ gas or material capable of generating $CO_2$ gas).

Figure 7:
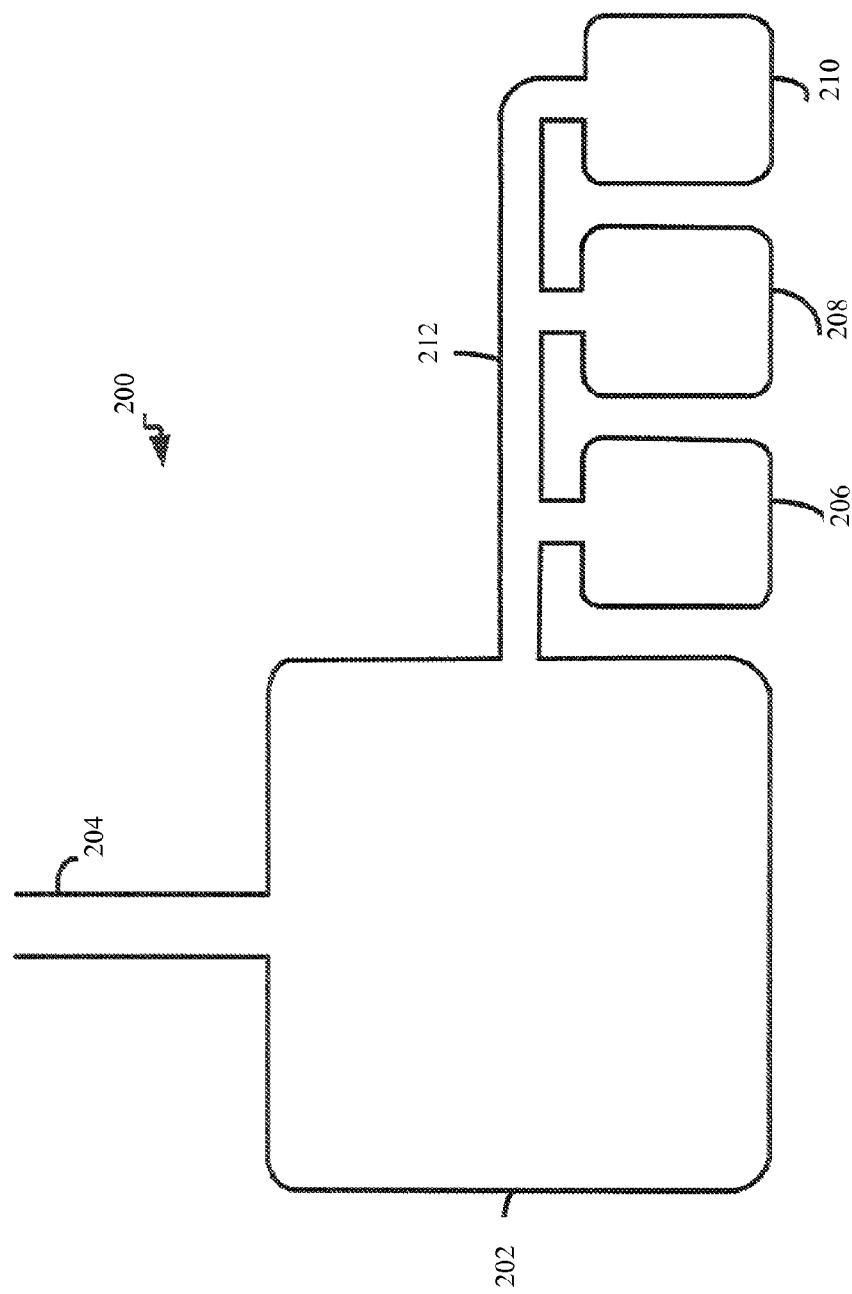
FIG. 7 is a front view of an exemplary platelet container system including a platelet container device fluidly attached to multiple satellite containers.

With reference to FIG. 7, platelet container system 200 can include a platelet container component 202 and an inlet port 204 configured to allow a platelet preparation to be inserted into platelet container component 202. Platelet container system 200 can include one or more satellite containers such as satellite containers 206, 208, and 210. Satellite containers 206, 208, and 210 can be fluidly connected to an inner region of platelet container component 202 via a channel 212 (e.g., a tube). In some cases, satellite containers 206, 208, and 210 can be fluidly connected to each other. One or more of the satellite containers can contain $CO_2$ gas or material capable of generating $CO_2$ gas. For example, satellite container 210 can contain $CO_2$ gas or material capable of generating $CO_2$ gas. In some cases, platelet container system 200 can include a valve or membrane configured to retain $CO_2$ gas or material capable of generating $CO_2$ gas within a satellite container until a user decides to allow the $CO_2$ gas or material capable of generating $CO_2$ gas to be released and moved into an inner region of platelet container component 202.

In some cases, a satellite container can be designed to house blood components such as red blood cells or plasma. For example, satellite container 206 can be designed to house red blood cells, and satellite container 208 can be designed to house plasma.

Figure 8:
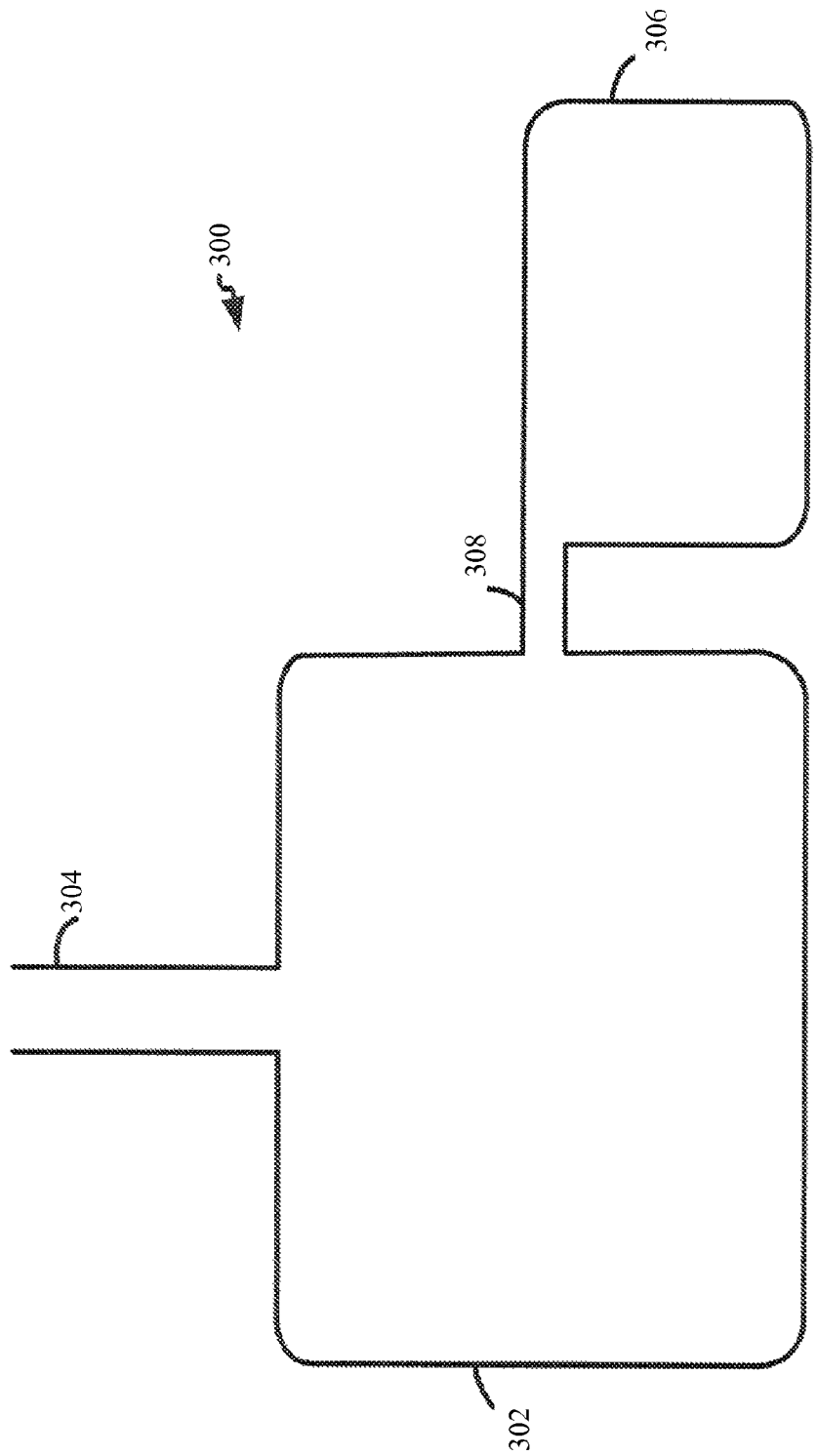
FIG. 8 is a front view of an exemplary platelet container system including a platelet container device fluidly attached to one satellite container.

With reference to FIG. 8, platelet container system 300 can include a platelet container component 302 and an inlet port 304 configured to allow a platelet preparation to be inserted into platelet container component 302. Platelet container system 300 can include one satellite container (e.g., satellite container 306). Satellite container 306 can be fluidly connected to an inner region of platelet container component 302 via a channel 308 (e.g., a tube). Satellite container 306 can contain $CO_2$ gas or material capable of generating $CO_2$ gas. In some cases, platelet container system 300 can include a valve or membrane configured to retain $CO_2$ gas or material capable of generating $CO_2$ gas within satellite container 306 until a user decides to allow the $CO_2$ gas or material capable of generating $CO_2$ gas to be released and moved into an inner region of platelet container component 302.

Figure 9:
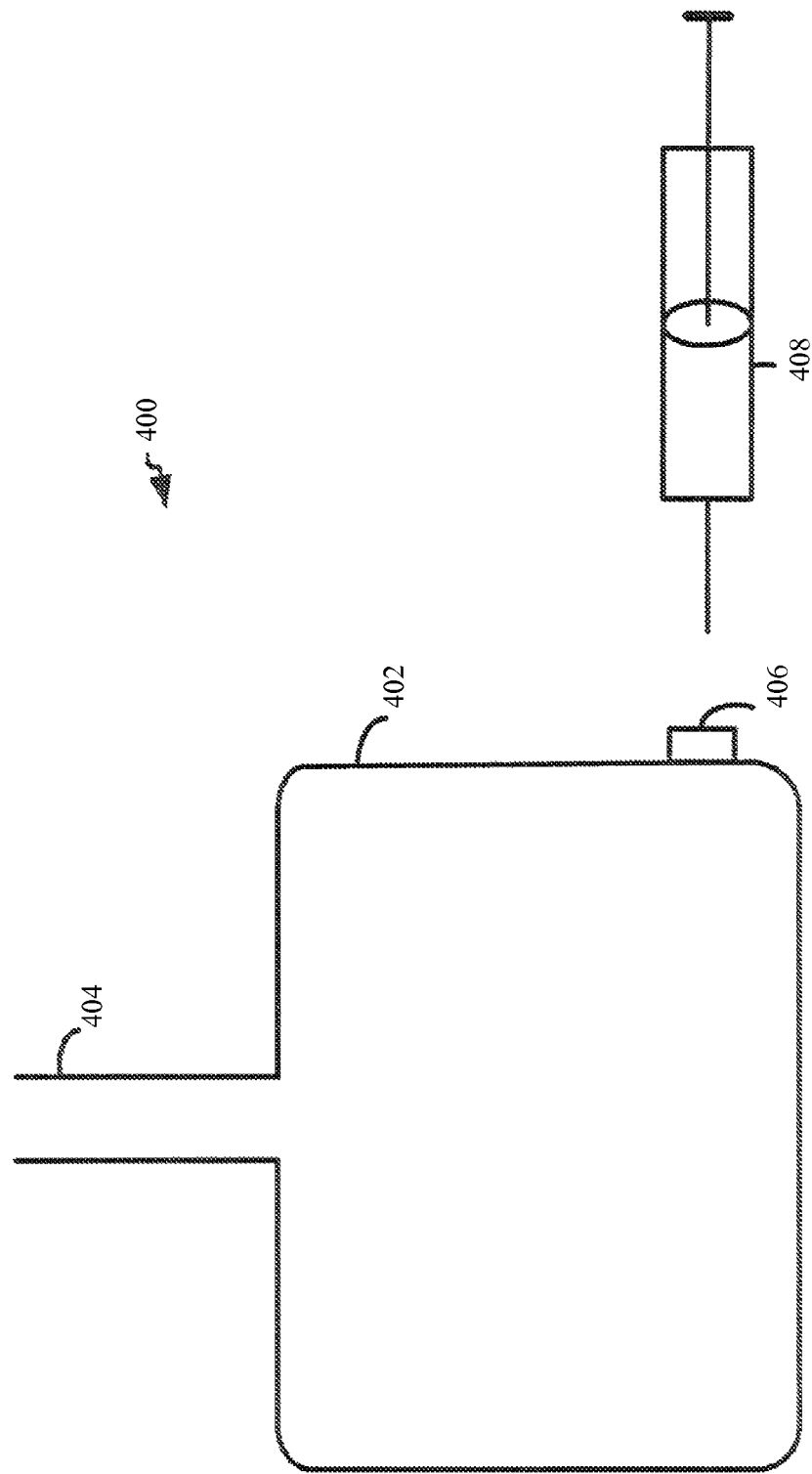
FIG. 9 is a front view of one example of a platelet container device having an injection port for sterilely injecting $CO_2$ gas or material capable of generating $CO_2$ gas into an inner region of the platelet container device.

In some cases, a platelet container component provided herein can include an injection port. For example, with reference to FIG. 9, a platelet container device 400 can include a platelet container component 402 and an inlet port 404 configured to allow a platelet preparation to be inserted into platelet container component 402. Platelet container device 400 can include an injection port 406. Injection port 406 can be configured to allow a needle (e.g., of a syringe 408) to be inserted into an inner region of platelet container component 402. The syringe can be used to deliver $CO_2$ gas or material capable of generating $CO_2$ gas into an inner region of platelet container component 402 in a sterile manner. In some cases, injection port 406 can be configured to seal upon removal of an inserted needle.

Figure 10:
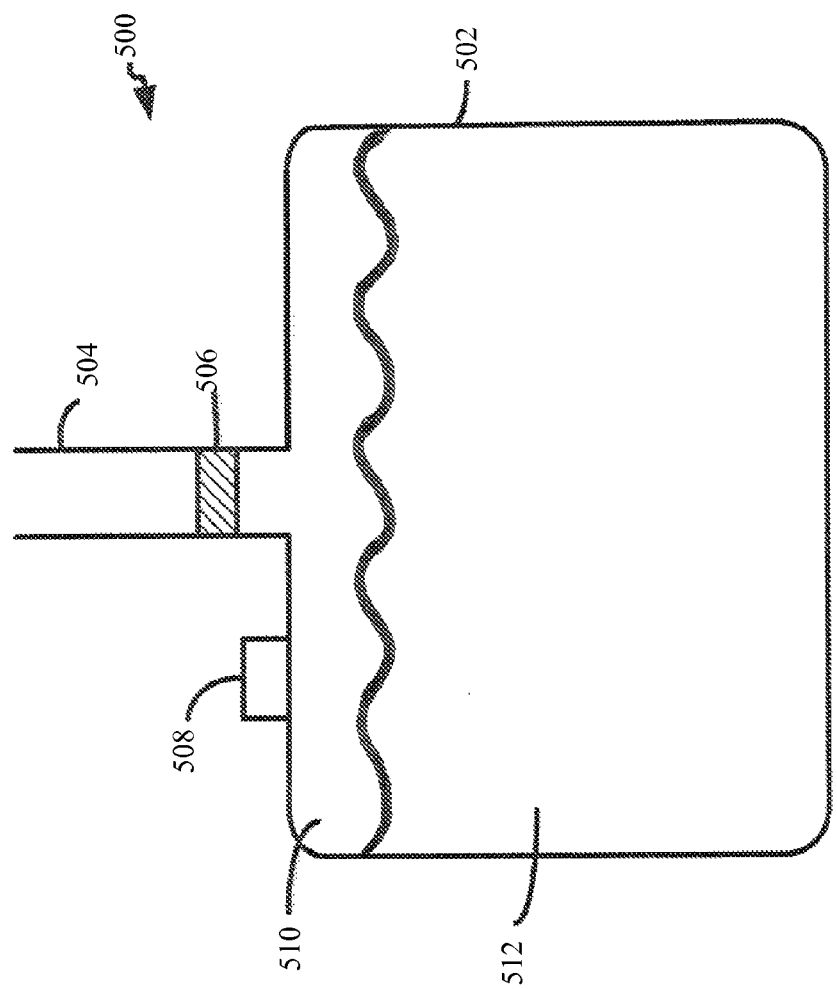
FIG. 10 is a front view of an exemplary platelet container device having an exhaust port for allowing gas to be removed from the inner region of the platelet container device.

In some cases, a platelet container component provided herein can include an exhaust valve. For example, with reference to FIG. 10, a platelet container device 500 can include a platelet container component 502 and an inlet port 504 configured to allow a platelet preparation 512 to be inserted into platelet container component 502. Platelet container device 500 can include an exhaust valve 508. Exhaust valve 508 can be configured to allow a user to remove gas 510 present within an inner region of platelet container component 502 in a sterile and sealable manner.

In some cases, a platelet container component provided herein can include an inlet port 504 having a valve. For example, with reference to FIG. 10, inlet port 504 can be configured to have valve 506. Valve 506 can be configured to have open and closed configurations. When in an open configuration, valve 506 can allow fluids and gases to pass into and out of an inner region of platelet container component 502. When in a closed configuration, valve 506 can prevent the contents within an inner region of platelet container component 502 from exiting that region via inlet port 504.

In some cases, a bag system can include a series of bags to facilitate the separation of blood into components. The blood can be first collected as whole blood (e.g., typically around 500 cubic centimeters) in a large bag, and other bags can receive the separated products during processing. In some cases, one of the bags not used in the initial collection of whole blood can be loaded with $CO_2$ for subsequent evacuation and mixing with the platelets. In some cases, a relatively small amount (e.g., 50-100 cubic centimeters) of $CO_2$ can be used to saturate the platelets completely.

In some cases, a bubble-like wrap-like reservoir with $CO_2$ can be incorporated into a platelet bag, and a simple one-way valve can be configured to permit evacuation of $CO_2$ with gentle squeezing into the remaining platelets. In some cases, a sterile one-way valve can be used to permit the rapid dosing of $CO_2$ from a traditional gas tank or other source. This can be configured in a manner that injects a known amount of $CO_2$ in the bag. Due to the nature of gas in closed spaces and equilibration characteristics of $CO_2$ and platelets, minimal mixing may be needed. In some cases, dry ice or another chemical reservoir that includes a phase change from solid to gas can be placed in the platelet bag to liberate $CO_2$.

In some cases, gases such as hydrogen sulfide (i.e., $H_2S$), HS, or isofluroane can be used in addition to $CO_2$ or in place of $CO_2$. For example, hydrogen sulfide can be used to store red blood cells or platelets as described herein using hydrogen sulfide in place of $CO_2$.

In some cases, red blood cells or platelets can be stored within a gas-impermeable container (e.g., a gas-impermeable bag such as a $CO_2$ gas impermeable bag made of PET) in the presence of $CO_2$ or another gas as described herein. In some cases, red blood cells or platelets can be stored within a gas-permeable container (e.g., a gas-permeable bag such as a current PL732 platelet bag) that can be stored within another container (e.g., a sealed cabinet) designed to have a particular amount of $CO_2$ or another gas such that the gas (e.g., $CO_2$ or another gas) can diffuse into the gas-permeable container housing the red blood cells or platelets.

Figure 14:
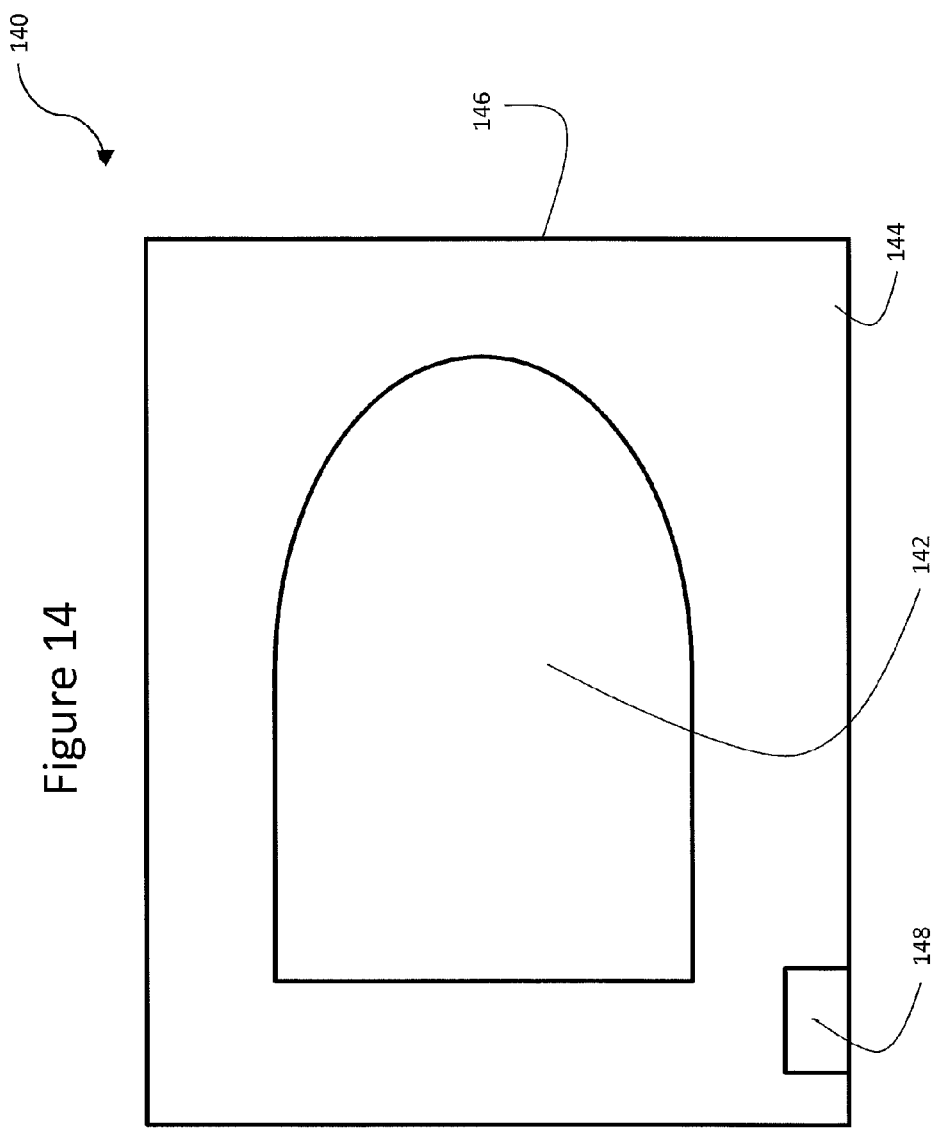
FIG. 14 is a front view of one example of a container having the ability to house one or more other smaller containers.

For example, with reference to FIG. 14, red blood cells or platelets can be stored within a gas-permeable container 142 (e.g., a gas-permeable bag such as a current PL732 platelet bag) that can be inserted into a larger container 144. Larger container 144 can be a gas-impermeable container (e.g., a gas-impermeable bag such as a $CO_2$ gas impermeable bag made of PET). Larger container 144 can include one or more openings or edges that allow a user to insert gas-permeable container 142 into larger container 144. In some cases, such one or more openings can be configured to allow a user to seal larger container 144 such that larger container 144 is gas-impermeable. For example, larger container 144 can include a sealable edge 146 that can be opened and closed to allow a user to insert gas-permeable container 142 into larger container 144 or to remove gas-permeable container 142 from larger container 144. In some cases, larger container 144 can be configured to contain one or more than one gas-permeable container(s) 142. For example, larger container 144 can be configured to contain two, three, four, five, six, seven, eight, nine, ten, or more gas-permeable containers. In some cases, larger container 144 can include an injection port 148 configured to allow a user to inject $CO_2$ gas or another gas into larger container 144.

Figure 15:
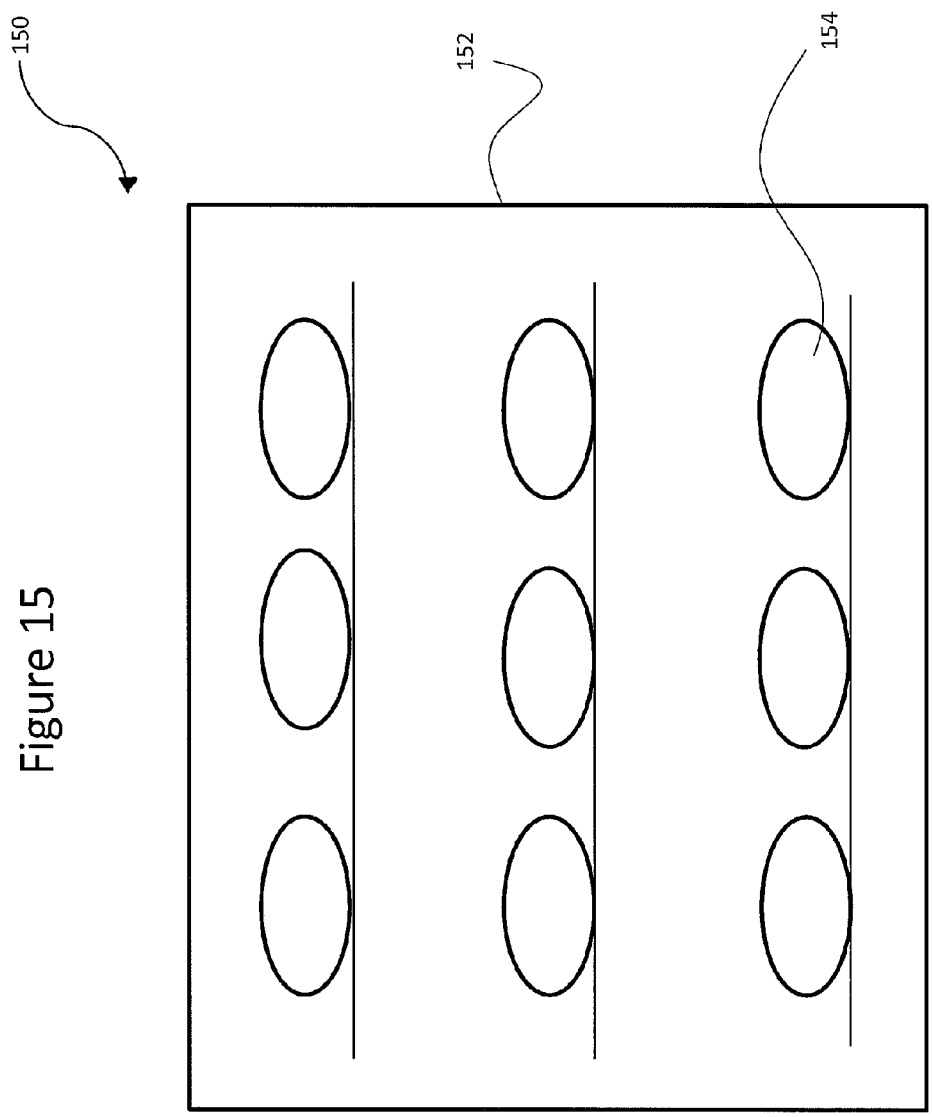
FIG. 15 is a front view of an inner region of a cabinet having the ability to house one or more containers.

In another example, with reference to FIG. 15, red blood cells or platelets can be stored within a gas-permeable container 154 (e.g., a gas-permeable bag such as a current PL732 platelet bag) that can be inserted into a cabinet 152. Cabinet 152 can be a gas-impermeable cabinet or chamber. Cabinet 152 can include a door that allows a user to insert gas-permeable container(s) 154 into cabinet 152 or remove gas-permeable container(s) 154 from cabinet 152. In some cases, such a door can be configured to allow a user to seal cabinet 152 such that cabinet 152 is gas-impermeable. In some cases, cabinet 152 can be configured to contain one or more than one gas-permeable container(s) 154. For example, cabinet 152 can be configured to contain two, three, four, five, six, seven, eight, nine, ten, or more gas-permeable containers. In some cases, cabinet 152 can be configured to inject $CO_2$ gas or another gas into the inner region of cabinet 152. In some cases, cabinet 152 can be configured to have a temperature-controlled environment within the cabinet. For example, cabinet 152 can include a temperature gauge and a cooling system such that a user can set an inner compartment of cabinet 152 to a particular temperature (e.g., between 10° C. and −5° C., between 5° C. and −1° C., between 4° C. and −2° C., between 1° C. and −1° C., or between 10° C. and 4° C.). In some cases, cabinet 152 can include $CO_2$ sensor to allow for the constant monitoring and control of $CO_2$ levels.

Figure 16:
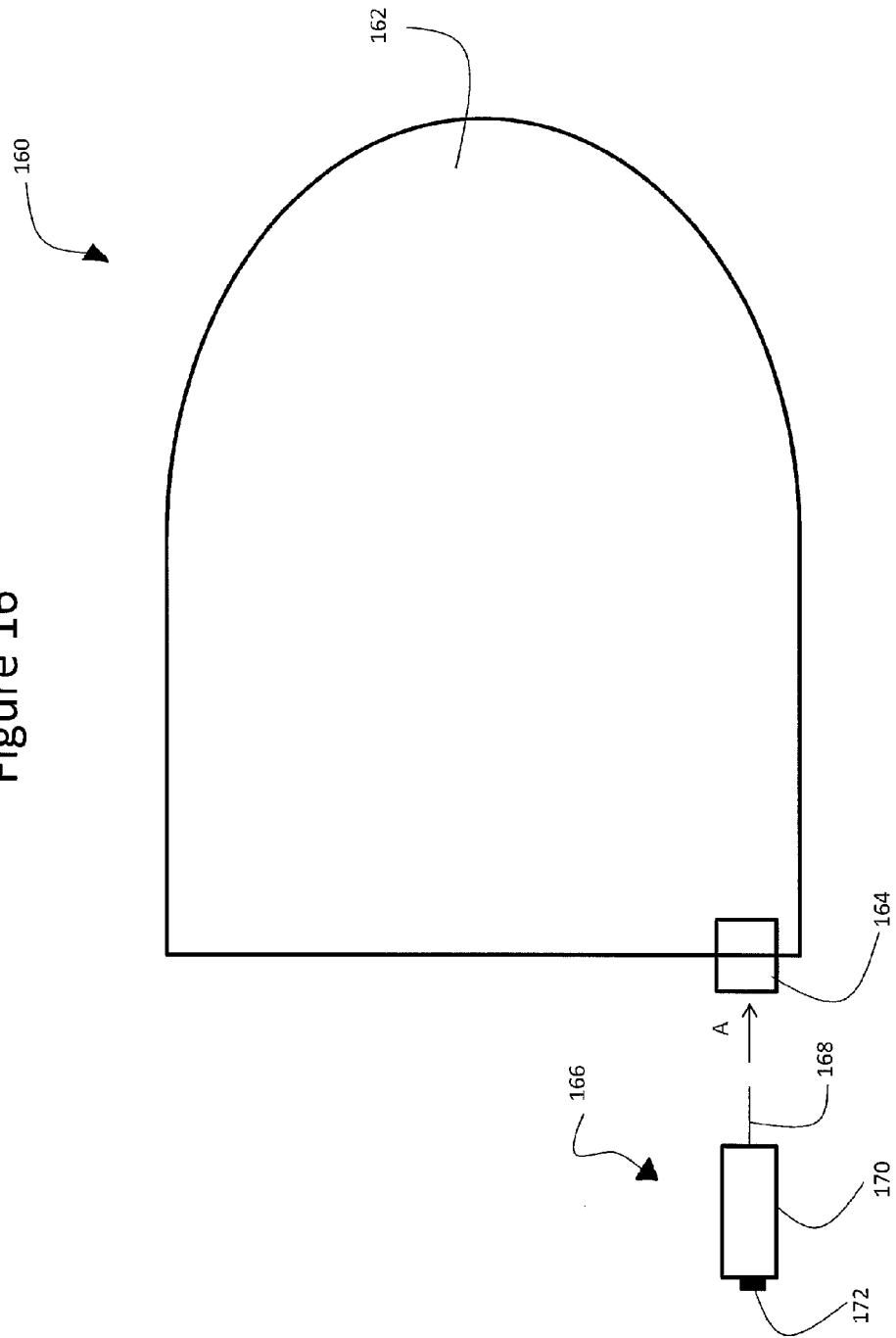
FIG. 16 is a front view of a container and a cartridge for injecting $CO_2$ or other gas into the container.

With reference to FIG. 16, red blood cells or platelets can be stored within a container 162. Container 162 can include an injection port 164 configured to allow a user to inject $CO_2$ gas or another gas into container 162. In some cases, a cartridge 166 having a needle portion 168 and a housing portion 170 can be pre-filled with $CO_2$ or another gas under pressure. In some cases, a luer lock fitting or other fitting can be used in place of needle portion 168. Cartridge 166 can include an actuator button or switch 172 configured to release the $CO_2$ or other gas. During use, a user can attach cartridge 166 to container 162 and press actuator button or switch 172 to inject $CO_2$ or another gas into container 162. The $CO_2$ or other gas can be injected pre- or post-blood collection.

Prior to use or release for use, a red blood cell or platelet preparation provided herein can be de-gassed or treated in a manner to remove a $CO_2$ gas or another gas. For example, a red blood cell or platelet preparation provided herein can be swirled over or in the presence of atmospheric air or $O_2$ (e.g., 100% $O_2$) until the pH of the preparation is greater than about 7.2 (e.g., until the pH of the preparation returns to a pH that is greater than pH 7.2). In some cases, room air or 100% oxygen can be used to reverse the pH to a level where the pH is above about 7.0 in around, for example, 5 to 20 minutes (e.g., about 10 minutes).

The invention will be further described in the following examples, which do not limit the scope of the invention described in the claims.

EXAMPLES

Example 1

Storing Red Blood Cells in the Presence of $CO_2$

Red blood cells were collected and processed using standard techniques and stored in standard blood bags. Prior to collecting the red blood cells, an empty blood bag containing anti-coagulated citrate phosphate dextrose with adenine (AS1) was flushed with $CO_2$ for one minute. The collection bag was then filled with blood from a donor. Next, 50 cubic centimeters of $CO_2$ were added to the bag via the sterile docking port. The bag was gently inverted for 30 seconds and then placed upright. Using an empty syringe, the 50 cubic centimeters of air/$CO_2$ was removed from the bag through the sterile docking port. The controls were red blood cell preparations placed in blood bags not flushed with $CO_2$ and not exposed to 50 cubic centimeters of $CO_2$.

The control and $CO_2$ treated red blood cell preparations were tested for $pCO_2$ (or $pO_2$) levels, lactate levels, glucose levels, and pH levels at days 0, 14, and 21 (Table 1). Storage with $CO_2$ resulted in a $pCO_2$ of >500 mmHg in the bag and a fall in pH to the 6.2 to 6.3 range (Table 1). This fall in pH is reversible, and pH levels can return to normal values of about 7.0 when normal $pCO_2$ levels (e.g., 40-60 mmHg) are re-established. Storage with $CO_2$ also resulted in an inhibition of lactate formation and glucose consumption as compared to the levels of lactate formation and glucose consumption exhibited in controls (Table 1).

TABLE 1

$pCO_2$ levels, lactate levels, glucose levels, and pH levels for red blood cell preparations exposed or not exposed to $CO_2$.

| Days | $pCO_2$ (mmHg) | | Lactate (μmol/mL) | | Glucose (mg/dL) | | pH | |
|---|---|---|---|---|---|---|---|---|
| | $CO_2$ Treated | Control | $CO_2$ Treated | Control | $CO_2$ Treated | Control | $CO_2$ Treated | Control |
| 0 | 527 | 53 | 1.2 | 1.2 | 571 | 571 | 6.2 | 7 |
| 14 | 528 | 56 | 5 | 9.4 | 503 | 419 | 6.2 | 7 |
| 21 | 501 | 49 | 5.3 | 17.82 | 478 | 187 | 6.2 | 6.8 |

These results demonstrate that storing red blood cells under conditions of greater than 100 mmHg of $pCO_2$ (e.g., greater than 200 mmHg of $pCO_2$, greater than 300 mmHg of $pCO_2$, greater than 400 mmHg of $pCO_2$, or greater than 500 mmHg of $pCO_2$) can inhibit glycolysis, suppress metabolism, and reduce oxidative stress, thereby prolonging the usable lifespan of the red blood cell preparation.

Example 2

Storing Platelets in the Presence of $CO_2$

Fresh human whole blood was drawn into 3.2% sodium citrate, and platelet-rich plasma (PRP) was prepared. Control citrated PRP was stored at room temperature in a polypropylene tube. $CO_2$ was exposed to the air/fluid interface of PRP using a 99.9% $CO_2$ tank. $CO_2$ was administered for approximately 60 seconds during which time the pH dropped from an average value of 7.4 to 6.4.

Figure 11:
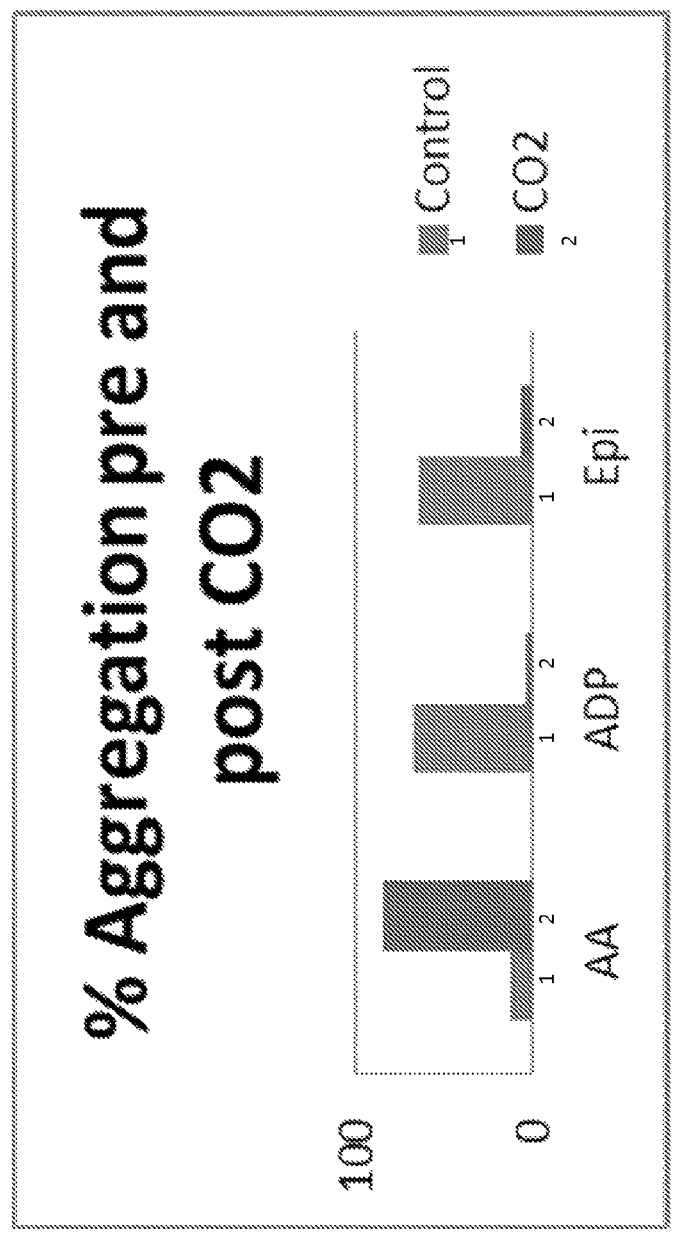
FIG. 11 is a graph plotting percent aggregation.

Using a Chronolog 700 platelet aggregometer, platelet aggregation was performed pre- and post-$CO_2$ to ADP, AA, and Epi. Platelet aggregometry was carried out as described elsewhere (Born and Cross, *J. Physiol.*, 168:178-195 (1963)). The assay was performed at 37° C. with a sample stir speed of 1200 r.p.m. Each sample consisted of 450 μL platelet rich plasma. The results are provided in FIG. 11.

Figure 12:
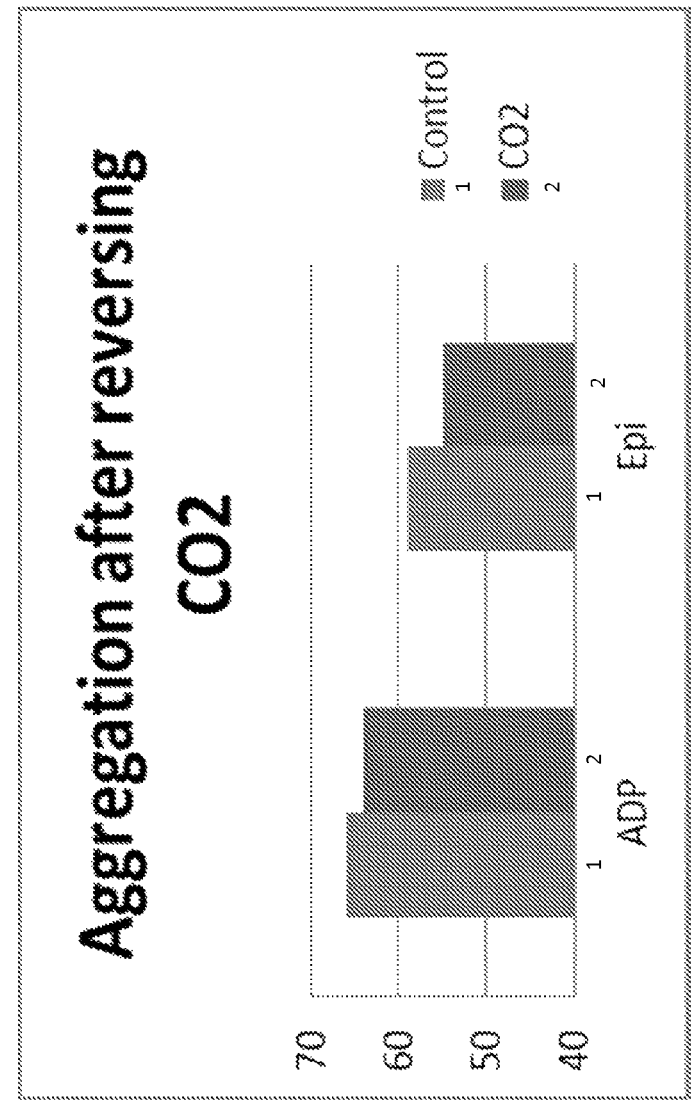
FIG. 12 is a graph plotting percent aggregation after reversing pH of $CO_2$ and control samples.

Aggregation was again recorded after reversing the $CO_2$ effect by adding atmospheric air into the PRP until the pH reached 7.2 (FIG. 12).

Figure 13:
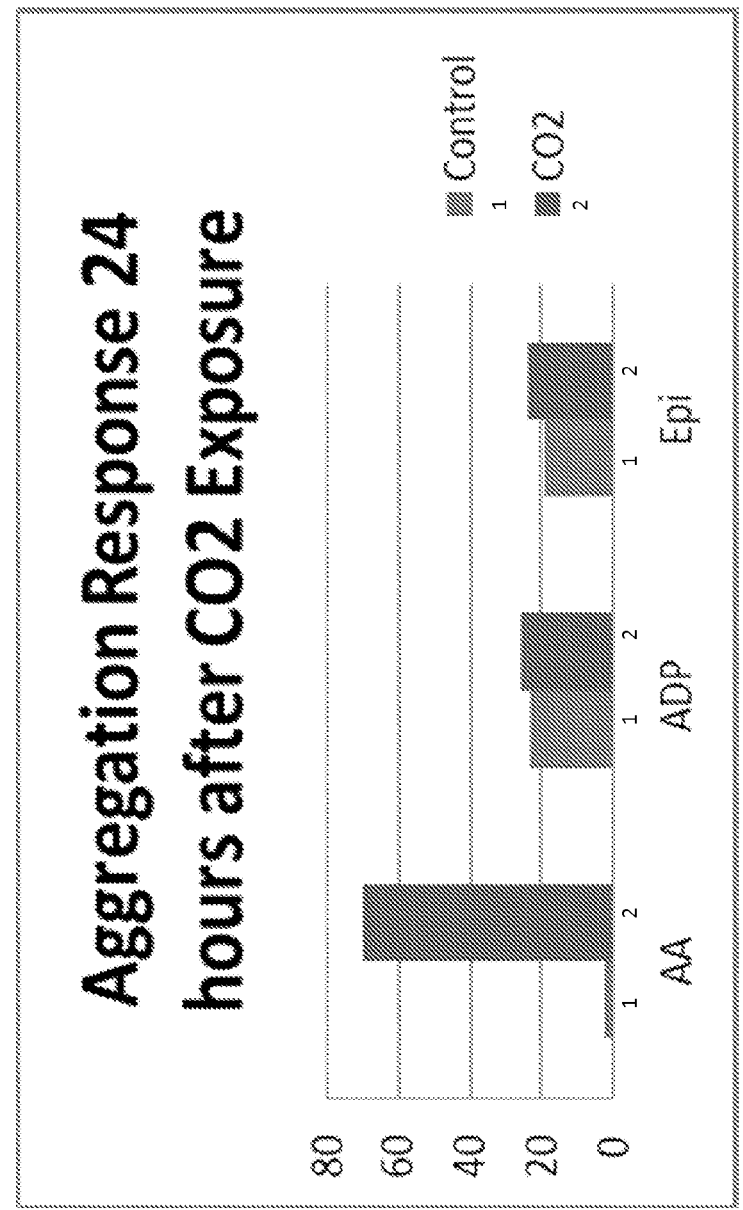
FIG. 13 is a graph plotting percent aggregation after 24 hours.

In addition, platelet aggregation was measured after 24 hours storage at room temperature for both the control and $CO_2$ treated group (FIG. 13).

Figure 18:
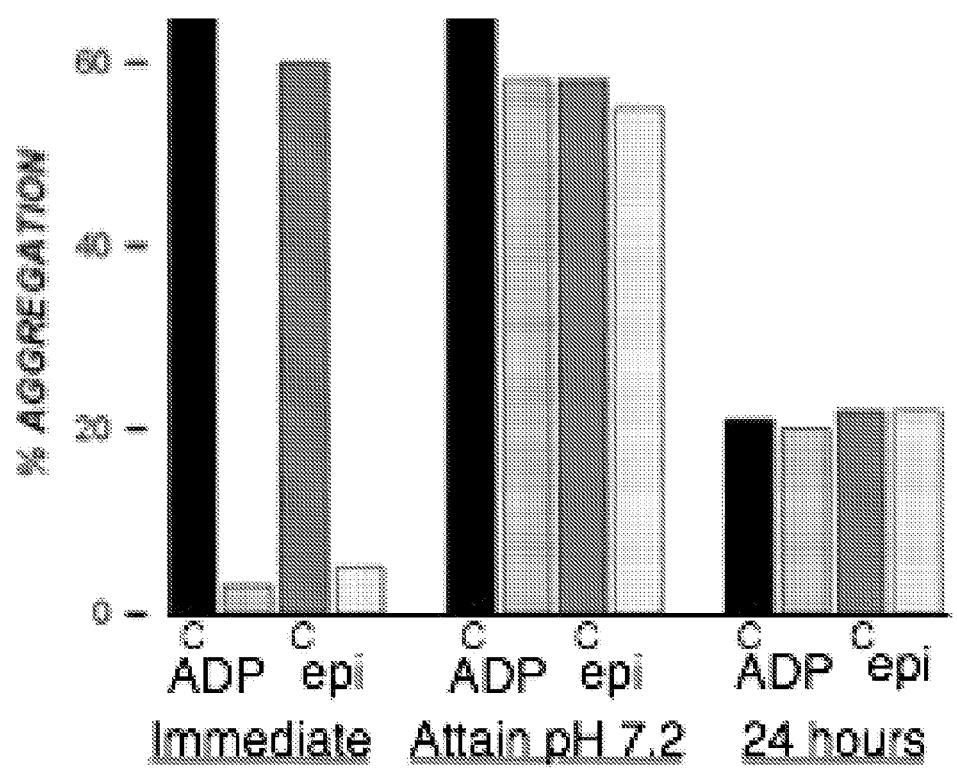
FIG. 18 is a bar graph plotting percent aggregation of platelets in PRP that were kept in room air (C) or in 99% $CO_2$ for 10 minutes or 24 hours. The 10 minute samples were assayed immediately or after they had re-attained pH 7.2. The 24-hour samples were assayed after the pH increased to 7.2.

In another study, the impact of $CO_2$ on platelet function was explored by equilibrating platelet-rich plasma (PRP) with 99% $CO_2$. The PRP was prepared by low-speed centrifugation of blood anticoagulated with 3.2% sodium citrate and kept in capped polypropylene tubes. Platelet function was measured by optical aggregometry with ADP and epinephrine as triggers. Equilibration with $CO_2$ under a positive flow of gas was monitored by the fall in pH from 7.2 to 6.4, which typically occurs within 60 seconds. Degassing of $CO_2$ by a flow of room air over the PRP was verified by the return to pH 7.2. Immediately after removal of the PRP from the $CO_2$ atmosphere, aggregation to ADP and epinephrine was suppressed (FIG. 18, first set). When the samples had returned to pH 7.2, aggregation to both triggers was restored (FIG. 18, center set). After 24 hours under $CO_2$, aggregation was equivalent to that of controls (FIG. 18, third set).

ATP Secretion Response Pre and Post $CO_2$

ATP secretion was performed using a Zylux luminometer where the secretion was induced using 1 μM thrombin. In this test, the ATP secretion rate and total ATP for the control group decreased significantly (to less than 15%) after 24 hours storage at room temperature. However, the $CO_2$ treated platelets had approximately 80% of baseline secretion after 24 hours storage. The $CO_2$ did not need to be reversed in order for the secretion response to proceed.

Bacterial Growth Inhibition Post $CO_2$

Clinical isolates of *Bacillus cereus* and *Pseudomonas aeruginosa* were spiked into control and $CO_2$ treated platelets at a concentration of 10 CFU (i.e., 10 bacteria total, not 10 CFU/mL). The platelets were stored for approximately 30 hours at room temperature on a platelet agitator. After 30 hours, quantitative culture was performed on serial dilutions of the platelet sample on 5% sheep blood agar plates.

*Bacillus cereus* grew to over ×10e5 CFU/mL for the control PRP, and no growth was observed for the sample containing *Bacillus cerus* exposed to $CO_2$. *Pseudomonas aeruginosa* grew to ×10e3 CFU/mL for the control PRP, whereas no growth occurred on the *Psudomonas aeruginosa* spiked PRP that was exposed to $CO_2$.

Example 3

Storing Platelets

Apheresis donor platelets, collected in PL732 citrate-dextrose-phosphate (CPD) platelet bags, using the Baxter/Fenwal Amicus Apheresis Instrumentation, are obtained in a routine manner following a transfusion protocol. These apheresis donor platelets undergo functional analyses in the presence and absence of $CO_2$ treatment. The following functional parameters are assessed on days 1 (day of collection) and 5 of storage: platelet activation, as indicated by an increase in the level of P-selectin expression; adenine nucleotide content, as determined by ATP levels and measured ATP release using bioluminescence; and platelet aggregation to 20 µM ADP, 10 µM epi, 0.4 mM AA, and collagen.

The bags (or segment tubes) of apheresis platelets are obtained from Mayo Transfusion Services. Each bag (or segment) of platelets is subsequently divided into a number of equal aliquots. The aliquots are stored on a platelet agitator at room temperature in sterile containers. Within 2 hours of obtaining the apheresis platelets, a number of samples are treated with $CO_2$, and a number of samples are used as controls. All samples are assayed for in vitro functional parameters.

Flow Cytometry for P-selectin Expression

Platelet activation is assessed using flow cytometry by monitoring P-selectin expression. Twenty µL of PC was diluted (100-fold) into a buffer containing 1 µm hirudin. The diluted blood samples are centrifuged for 10 minutes at 1000 g. Supernatants are discarded, and the cell pellets are resuspended in buffer. Diluted whole-blood samples (100 µL) are activated with human thrombin (10.0 nM for 10 minutes; Haematologic Technologies, Essex Junction, Vt.) and are stained simultaneously for glycoprotein β3 and P-selectin (30 minutes) using mouse monoclonal immunoglobulin G (IgG) against P-selectin (CD62) conjugated to phycoerythrin (PE) and mouse monoclonal IgG against glycoprotein IIbIIIa (CD61) conjugated to fluorescein isothiocyanate (FITC) (Becton-Dickinson, San Jose, Calif.). Each sample is fixed by the addition of 100 µL of a 1:20 dilution of formalin for 30 minutes and then is neutralized with 0.2 M Tris, to a pH of 8.0. Samples are then diluted down to 2 mL for analysis. Samples are analyzed using a Partec (Muenster, Germany) CA3 flow cytometer.

Bioluminescence for ATP Secretion

Apheresis platelets, with and without CO2 exposure, are assayed for the rate of dense body ATP secretion and total platelet ATP content using a custom designed luminometer. Platelet ATP secretion is measured by adding luciferase (1 mg/mL) and luciferin (10 µg/mL) to each sample (Owen et al., *Biochemistry*, 34:9277-9281 (1995) and Kahn et al., *Nature*, 394:690-694 (1998)). The luminescence generated by platelet release of ATP is compared with that of an ATP standard. For each assay, 40 mL of platelets diluted 1:1000 is mixed with 10 mL of luciferase reagent (0.5 mg/mL luciferase, 1.4 mg/mL luciferin) (Sigma Chemical Co., St Louis, Mo.) and is placed in a photomultiplier tube compartment. Diluted platelets are activated with 50 µL of 10.0 nM human alpha-thrombin. Data are acquired using an OLIS (OLIS, Bogart, Ga.) interface and software.

Response is measured as rate of ATP secretion by plotting the slope of the secretion curve vs. time. Total ATP content is measured as the amount of ATP released after lysis of cells using a detergent (50 µL of a 1:100 dilution of Triton-X-100). Without the ability to aggregate, platelets are unable to form effective haemostatic plugs, which are necessary to control active and chronic bleeding. The relative response of platelets to various agonists is routinely measured photometrically (Chronolog Corp., Havertown, Pa.). Each platelet sample is challenged with an agonist to promote aggregation, as evidenced by clumping. Once a platelet aggregate forms, more light is able to pass through the sample. The amount of light passing though is measured by photometric analysis. An increase in the level of platelet aggregation is manifest as an increase in light emission, with its relative intensity recorded by a turbidometer. Weak aggregation allows relatively less light to pass through, and no aggregation allows little or no light to pass above the baseline level.

Data analyses of the results of all samples assessing functional parameters are reported as percentage change, mean, or observed change. When appropriate, the data analysis for each assessed parameter between both groups (experimental preservative solution-treated vs. untreated) is performed using a paired Student's t-test.

Bacterial Growth by Traditional Culture

The impact of $CO_2$ on apheresis collected platelets is evaluated for the following 15 microorganisms: *Bacillus cereus, Bacillus subtilis, Clostridium perfringens, Corynebacterium species, Echerichia coli, Enterobacter cloacae, Klebsiella oxytoca, Propionibacterium acnes, Pseudomonas aeruginosa, Serratia marcescens, Staphylococcus aureus, Staphylococcus epidermidis, Streptococcus pyogenes*, viridans group *Streptococcus* species, and *Candida albicans*. For each isolate, colonies are inoculated from the 5% sheep blood agar plate into Tryptic Soy Broth (TSB) at $5 \times 10^7$ to $1 \times 10^8$ CFU/mL (0.5-1.0 McFarland standard). A 1:100 dilution is made into 20 mL TSB for inoculating into platelets (~$10^6$ CFU/mL) to yield a bacteria stock.

Leukoreduced Apheresis Platelet (LRAP) units obtained from Mayo Transfusion Services blood bank are inoculated with bacteria at an approximate concentration of 100 bacteria. A 50 mL LRAP unit aliquot will be spiked with 10 microliters of a single organism bacterial stock to yield a final concentration of 1-10 CFU/mL. Initial concentration of spike and grow inoculums are quantified via traditional culture. Additionally, an uninoculated LRAP aliquot is preserved for bacterial growth determination. Inoculated LRAP aliquots are maintained in a platelet agitator at 22-25° C. for 24 hours. Following the incubation period, 1 mL samples of each spiked LRAP aliquot are collected, and the remaining spiked sample is left in incubation for an additional 24 hours to screen for slow growing organisms.

Example 4

Inhibition of Bacterial Growth within Platelet Preparations Stored Under $CO_2$ Conditions Outdated apheresis platelet unit (day 6) was obtained from the Mayo Clinic components laboratory. About half of the platelet unit was perfused with 99% $CO_2$ gas for 10 minutes with mixing. Control samples without $CO_2$ exposure and $CO_2$-treated samples of 10 mL volume were inoculated with clinical isolates of eight different organisms. Control and $CO_2$ samples were spiked with identical bacterial loads. Quantitative culture using 5% sheep blood agar plates was conducted immediately following inoculation (0 hours) and at 24 and 48 hour time points. Time 0 hour inoculation load was selected to compensate for observed "spike and die" in outdated apheresis platelet units. The time 0 hour value represented the value of the initial spike.

Figure 17:
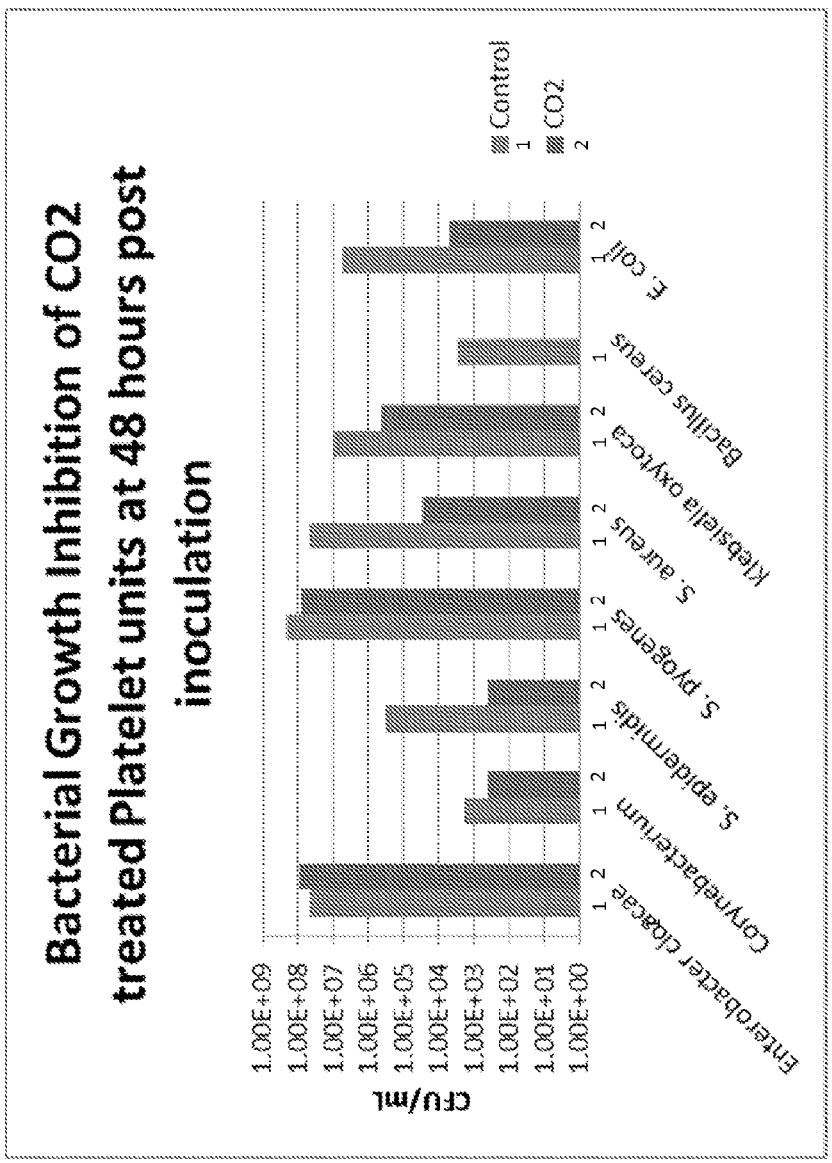
FIG. 17 is a graph plotting bacterial growth (CFU/mL) of the indicated bacteria 48 hour after inoculation within either a preparation of control platelets or a preparation of platelets exposed to 99% $CO_2$ gas.

Bacterial growth was reduced for those samples exposed to 99% $CO_2$ gas for 10 minutes (Table 2 and FIG. 17).

TABLE 2

| | Control | | | $CO_2$ | | |
|---|---|---|---|---|---|---|
| Organism | 0 hours | 24 hours | 48 hours | 0 hours | 24 hours | 48 hours |
| S. epidermidis | 5.10E+02 | 1.41E+03 | 3.30E+05 | 6.10E+02 | 3.30E+02 | 4.20E+02 |
| S. pyogenes | 1.67E+03 | 1.12E+06 | 2.10E+08 | 1.55E+03 | 1.20E+05 | 8.00E+07 |
| S. aureus | 1.14E+03 | 3.40E+05 | 4.80E+07 | 1.17E+03 | 3.20E+03 | 2.70E+04 |
| Klebsiella oxytoca | 9.80E+02 | 6.60E+05 | 1.00E+07 | 8.10E+02 | 1.15E+04 | 4.30E+05 |
| Bacillus cereus | 5.00E+01 | 8.00E+01 | 2.90E+03 | 1.00E+01 | no growth | no growth |
| E. coli | 4.00E+01 | 2.70E+03 | 5.50E+06 | 1.00E+01 | 1.80E+02 | 5.20E+03 |
| Enterobacter cloacae | 1.10E+03 | 9.90E+05 | 4.70E+07 | 1.22E+03 | 1.20E+06 | 8.60E+07 |
| Corynebacterium | 3.20E+02 | 2.30E+02 | 1.90E+03 | 7.90E+02 | 2.70E+02 | 4.20E+02 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a platelet concentrate, the method comprising:
exposing a platelet concentrate to $CO_2$ gas under conditions wherein the $pCO_2$ level of said platelet concentrate is about 150 mmHg of $pCO_2$ to about 600 mmHg of $pCO_2$.

2. The method of claim 1, wherein said method comprises exposing said platelet concentrate to $CO_2$ gas under conditions wherein the $pCO_2$ level of said platelet concentrate is about 200 to about 600 mmHg of $pCO_2$.

3. The method of claim 1, wherein the $pCO_2$ of said platelet concentrate is about 450 to about 550 mmHg of $pCO_2$.

4. The method of claim 1, wherein the method performs at least one of a) reducing platelet metabolism, b) preserving platelet function, and c) reducing the risk of bacterial contamination.

5. The method of claim 1, wherein exposing said platelet concentrate to $CO_2$ gas brings the pH of the platelet concentrate to equal to or less than about 6.4.

6. The method of claim 1, wherein an ATP secretion rate of the platelet concentrate induced by about 1 μM thrombin after about 24 h storage is approximately 80% or more of the ATP secretion rate induced by about 1 μM thrombin before the storage.

7. The method of claim 1, wherein a growth rate of about 10 CFU bacteria in the platelet concentrate after about 30 hours storage at room temperature is about zero.

8. The method of claim 1, wherein the exposing comprises exposing to $CO_2$ for at least about 10 minutes.

9. The method of claim 1, wherein the exposing comprises exposing to $CO_2$ for at least about 10 minutes, wherein after the exposure to the $CO_2$, bacterial growth after about 1 day as compared to a corresponding platelet concentrate without the exposure to $CO_2$ is about 80 to about 1,000,000 CFU/(mL*day) less.

10. The method of claim 1, wherein the exposing comprises exposing to $CO_2$ for at least about 10 minutes, wherein after the exposure to the $CO_2$, bacterial growth after about 2 days as compared to a corresponding platelet concentrate without the exposure to $CO_2$ is about 975 to about 65,000,000 CFU/(mL*day) less.

11. A method of treating a platelet concentrate, the method comprising:
exposing a platelet concentrate to CO2 gas under conditions wherein the pH of said platelet concentrate is equal to or less than about 6.4 and the pCO2 of said platelet concentrate is about 200 to about 600 mmHg of pCO2.

12. The method of claim 11, wherein the $pCO_2$ of said platelet concentrate is about 450 to about 550 mmHg of $pCO_2$.

13. The method of claim 11, wherein the method performs at least one of a) reducing platelet metabolism, b) preserving platelet function, and c) reducing the risk of bacterial contamination.

14. The method of claim 11, wherein an ATP secretion rate of the platelet concentrate induced by about 1 μM thrombin after about 24 h storage is approximately 80% or more of the ATP secretion rate induced by about 1 μM thrombin before the storage.

15. The method of claim 11, wherein a growth rate of about 10 CFU bacteria in the platelet concentrate after about 30 hours storage at room temperature is about zero.

16. The method of claim 11, wherein the exposing comprises exposing to $CO_2$ for at least about 10 minutes.

17. The method of claim 11, wherein the exposing comprises exposing to $CO_2$ for at least about 10 minutes, and wherein after the exposure to the $CO_2$ bacterial growth after about 1 day as compared to a corresponding platelet concentrate without the exposure to $CO_2$ is about 80 to about 1,000,000 CFU/(mL*day) less.

18. The method of claim 11, wherein the exposing comprises exposing to $CO_2$ for at least about 10 minutes, and wherein after the exposure to the $CO_2$ bacterial growth after about 2 days as compared to a corresponding platelet concentrate without the exposure to $CO_2$ is about 975 to about 65,000,000 CFU/(mL*day) less.

19. A method for treating a platelet concentrate, the method comprising:

exposing a platelet concentrate to $CO_2$ gas for at least about 10 minutes under conditions wherein the $pCO_2$ level of said platelet concentrate is greater than about 200 mmHg to about 600 mmHg of $pCO_2$ and the pH of said platelet concentrate is equal to or less than about 6.4, wherein after the exposure to the $CO_2$, bacterial growth after about 1 day as compared to a corresponding platelet concentrate without the exposure to $CO_2$ is about 80 to about 1,000,000 CFU/(mL*day) less, and bacterial growth after about 2 days as compared to a corresponding platelet concentrate without the exposure to $CO_2$ is about 975 to about 65,000,000 CFU/(mL*day) less.

* * * * *